US012044677B2

(12) United States Patent
Travis et al.

(10) Patent No.: US 12,044,677 B2
(45) Date of Patent: *Jul. 23, 2024

(54) METHODS AND TEST KITS FOR DETERMINING MALE FERTILITY STATUS

(71) Applicant: Androvia LifeSciences, LLC, Mountainside, NJ (US)

(72) Inventors: Alexander J. Travis, Ithaca, NY (US); Cristina Cardona, Highland Park, NJ (US); Melissa A. Moody, Brick, NJ (US); Alana J. Simpson, Summit, NJ (US); G. Charles Ostermeier, Gillette, NJ (US)

(73) Assignee: Androvia LifeSciences, LLC, Mountainside, NJ (US)

( * ) Notice: Subject to any disclaimer, the term of this patent is extended or adjusted under 35 U.S.C. 154(b) by 461 days.

This patent is subject to a terminal disclaimer.

(21) Appl. No.: 16/714,319

(22) Filed: Dec. 13, 2019

(65) Prior Publication Data

US 2020/0116707 A1    Apr. 16, 2020

Related U.S. Application Data

(63) Continuation of application No. 15/435,875, filed on Feb. 17, 2017, now Pat. No. 10,539,555.

(60) Provisional application No. 62/328,890, filed on Apr. 28, 2016, provisional application No. 62/322,252, filed on Apr. 14, 2016, provisional application No. 62/296,420, filed on Feb. 17, 2016.

(51) Int. Cl.
*G01N 33/50* (2006.01)
*G01N 1/30* (2006.01)
*G01N 21/64* (2006.01)
*G01N 33/92* (2006.01)

(52) U.S. Cl.
CPC ..... *G01N 33/5091* (2013.01); *G01N 21/6428* (2013.01); *G01N 33/92* (2013.01); *G01N 1/30* (2013.01); *G01N 2021/6439* (2013.01); *G01N 2405/10* (2013.01); *G01N 2800/367* (2013.01)

(58) Field of Classification Search
CPC .. G01N 33/5091; G01N 21/6428; G01N 1/30; G01N 2021/6439; G01N 2405/10; G01N 2800/367
See application file for complete search history.

(56) References Cited

U.S. PATENT DOCUMENTS

| | | | |
|---|---|---|---|
| 5,994,086 A | 11/1999 | Benoff | |
| 6,258,525 B1 | 7/2001 | Benoff | |
| 6,627,655 B2 | 9/2003 | D'Cruz et al. | |
| 6,835,717 B2 | 12/2004 | Hildreth | |
| 7,160,676 B2 | 1/2007 | Travis et al. | |
| 7,670,763 B2 | 3/2010 | Travis et al. | |
| 8,367,313 B2 | 2/2013 | Travis et al. | |
| 2002/0064849 A1 | 5/2002 | Herr et al. | |
| 2004/0038424 A1 | 2/2004 | Maples | |
| 2005/0037334 A1 | 2/2005 | Travis et al. | |
| 2007/0105188 A1 | 5/2007 | Travis et al. | |
| 2010/0248302 A1 | 9/2010 | Travis et al. | |
| 2010/0291536 A1 | 11/2010 | Viljoen et al. | |

FOREIGN PATENT DOCUMENTS

| | | |
|---|---|---|
| CA | 2533542 A1 | 2/2005 |
| TW | 201629488 A | 8/2016 |
| WO | 2003100025 A2 | 12/2003 |
| WO | 20050099222 A2 | 2/2005 |
| WO | 2008142396 A1 | 11/2008 |
| WO | 2016044392 A1 | 3/2016 |

OTHER PUBLICATIONS

Extended European Search Report of EP 17753900 dated Nov. 26, 2019 (8 pages).
First Office Action issued Apr. 29, 2021 for Chinese Patent Application No. 201780024041.6; 24 pages.
Amaya et al., "Production of Transgenic Xenopus laevis by Restriction Enzyme Mediated Integration and Nuclear Transplantation", J. Vis. Exp., vol. 42, e2010, doi:10.3791/2010 (2010).
Cross, "Effect of Methyl-B-Cyclodextrin on the Acrosomal Responsiveness of Human Sperm", Molecular Reproduction and Development, vol. 53, pp. 92-98 (1999).
Ensrud et al., "Immunocytochemical Studies on Co-Localization of the Ganglioside GM1 and Maturation Protein D (Crisp 1) on Sperm Suggests the Presence of Lipid Rafts in Rat Sperm Plasma Membranes", Molecular Biology of the Cell, Supplement to Molecular Biology of the Cell, vol. 11, 520a (2000).
Obembe et al., "Implication of Hongres1 Protein in Quassin-Induced Male Reproductive Abnormality in Rats", Endocrinol Metab Synd, vol. 3, No. 128 doi: 10,4172/2161-1017.1000128 (2014).
Selvaraj et al., "Gm1 Dynamics as a Marker for Membrane Changes Associated with the Process of Capacitation in Murine and Bovine Spermatozoa", Journal of Andrology, vol. 28, No. 4, pp. 588-599, 2007.
Travis et al., "Expression and Localization of Caveolin-1, and the Presence of Membrane Rafts, in Mouse and Guinea Pig Spermatozoa", Developmental Biology, vol. 240, pp. 599-610 (2001).

(Continued)

*Primary Examiner* — Changhwa J Cheu
(74) *Attorney, Agent, or Firm* — Morgan, Lewis & Bockius LLP

(57) ABSTRACT

This disclosure provides a method for determining male fertility status. The method comprises determining $G_{M1}$ localization patterns following induced sperm capacitation, identifying the percentage of various patterns, particularly the ratio of [(AA+APM)/total number of $G_{M1}$ localization patterns] and determining if the percentage of certain $G_{M1}$ localization patterns in response to induced capacitation is altered. Based on the change in the percentage of localization patterns of certain patterns in response to induced capacitation, alone or in combination with other sperm attributes, male fertility status can be identified.

26 Claims, 6 Drawing Sheets

(56) References Cited

OTHER PUBLICATIONS

Travis et al., "Functional Relationships between Capacitation-dependent Cell Signaling and Compartmentalized Metabolic Pathways in Murine Spermatozoa", The Journal of Biological Chemistry, vol. 276, No. 10, pp. 7630-7636 (2001).
International Search Report for PCT/US16/68204 dated May 11, 2017.
Written Opinion for PCT/US16/68204 dated May 11, 2017.
International Search Report for PCT/US2017/018325 dated May 4, 2017.
Written Opinion for PCT/US2017/018325 dated May 4, 2017.
Office Action issued Jan. 12, 2022 for Japanese Patent Application No. 2020-24269; 5 pages.
Office action dated Jan. 5, 2021 in connection with Taiwanese Patent Application No. 106105366.
Office action dated Jan. 5, 2021 in connection with Japanese Patent Application No. 2018543191.
Patent examination report 1 dated Apr. 1, 2022, for New Zealand Patent Application No. 745219; 4 pages.
Examination report No. 1 issued Aug. 16, 2022 in connection with Australian Patent Application No. 2017220013 (4 pages).
Office Action for related Korean Application No. 10-2018-7026493 dated Jul. 11, 2022, 4 pages.
Office Action dated Jun. 7, 2022, for Mexican Patent Application No. MX/a/2018/010003; 5 pages.
Office Action dated Jul. 11, 2022, for South Korean Patent Application No. 10-2018-7026493; 5 pages.
Search report No. 1 issued Nov. 3, 2022 in connection with Taiwan Patent Application No. 110145620 (7 pages).

METHODS AND TEST KITS FOR DETERMINING MALE FERTILITY STATUS

CROSS-REFERENCE TO RELATED APPLICATIONS

This application is a continuation of U.S. patent application Ser. No. 15/435,875, filed Feb. 17, 2017, which claims the benefit of U.S. Provisional Application No. 62/296,420, filed on Feb. 17, 2016, U.S. Provisional Application No. 62/322,252, filed Apr. 14, 2016, U.S. Provisional Application No. 62/328,890 filed Apr. 28, 2016, each of which is incorporated in its entirety.

FIELD OF THE DISCLOSURE

This invention relates generally to the field of male fertility and more specifically to determining male fertility status based on $G_{M1}$ ganglioside distribution patterns following induced sperm capacitation.

BACKGROUND OF THE DISCLOSURE

In the US, 10% of couples have medical appointments related to infertility with 40% of infertility being associated with the male. Globally, this translates to over 73 million infertile couples. Typical male reproductive health exams assess sperm number, appearance, and motility. Unfortunately, half of infertile men have sperm that meet normal parameters for these descriptive criteria and are only identified as having "idiopathic infertility" after repeatedly failing at both natural conception and techniques of assisted reproduction such as intra-uterine insemination (IUI). Because each failed cycle inflicts great physical, emotional, and financial tolls on couples and it costs the US healthcare system over $5 billion annually, there is a tremendous need for a practical test of sperm function. Data on sperm function would allow clinicians to direct their patients toward a technology of assisted reproduction that would give them the best chance to conceive.

Upon entrance into the female tract, sperm are not immediately able to fertilize an egg. Rather, they must undergo a process of functional maturation known as "capacitation." This process relies upon their ability to respond to specific stimuli by having specific changes in their cell membrane, namely a change in the distribution pattern of the ganglioside $G_{M1}$ in response to exposure to stimuli for capacitation.

Various $G_{M1}$ localization patterns have been identified and associated with capacitation or non-capacitation. In particular, apical acrosome (AA) $G_{M1}$ localization patterns and acrosomal plasma membrane (APM) $G_{M1}$ localization patterns have been associated with capacitation in bovine and human sperm. Sperm capacitation can be quantitatively expressed as a Cap-Score™ value, generated via the Cap-Score™ Sperm Function Test ("Cap-Score™ Test" or "Cap-Score"), is defined as ([number of apical acrosome (AA) $G_{M1}$ localization patterns+number of acrosomal plasma membrane (APM) $G_{M1}$ localization patterns]/total number of $G_{M1}$ labeled localization patterns) where the number of each localization pattern is measured and then ultimately converted to a percentage score. In addition to APM $G_{M1}$ localization patterns and AA $G_{M1}$ localization patterns, the other labeled localization patterns included Lined-Cell $G_{M1}$ localization patterns, intermediate (INTER) $G_{M1}$ localization patterns, post acrosomal plasma membrane (PAPM) $G_{M1}$ localization patterns, apical acrosome/post acrosome (AA/PA) $G_{M1}$ localization patterns, equatorial segment (ES) $G_{M1}$ localization patterns, and diffuse (DIFF) $G_{M1}$ localization patterns. (Travis et al., "Impacts of common semen handling methods on sperm function," The Journal of Urology, 195 (4), e909 (2016)).

SUMMARY OF THE DISCLOSURE

In one embodiment, disclosed herein are methods and kits for determining male fertility status. In one embodiment, this disclosure describes a method for identifying male fertility status based on a change in the number of certain $G_{M1}$ localization patterns in response to induced in vitro capacitation. In one embodiment, the $G_{M1}$ localization pattern is a Lined-Cell $G_{M1}$ localization pattern.

An embodiment disclosed herein is a method for determining male fertility status. In one embodiment, the method comprising the following steps. A sample of in vitro capacitated sperm cells is treated with a fluorescence label. One or more capacitated-fluorescence images is obtained wherein the images display one or more $G_{M1}$ localization patterns associated with fluorescence labeled in vitro capacitated sperm cells. An apical acrosome (AA) $G_{M1}$ localization pattern and an acrosomal plasma membrane (APM) $G_{M1}$ localization pattern are each assigned to a capacitated state and a Lined-Cell $G_{M1}$ localization pattern and all other labeled $G_{M1}$ localization patterns are assigned to a non-capacitated state each displayed in the capacitated-fluorescence images. A number for $G_{M1}$ localization patterns is measured, the patterns comprising AA $G_{M1}$ localization pattern, APM $G_{M1}$ localization pattern, Lined-Cell $G_{M1}$ localization pattern and all other labeled $G_{M1}$ localization patterns, for the fluorescence labeled in vitro capacitated sperm cells, displayed in the capacitated-fluorescence images to determine a percentage of [(AA $G_{M1}$ localization patterns plus APM $G_{M1}$ localization patterns)/total $G_{M1}$ localization patterns]. In one embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage than one standard deviation below the reference mean percentage indicates fertile; less than a percentage that is one standard deviation below the reference mean percentage and greater than a percentage that is two standard deviations below the reference mean percentage indicates sub-fertile; less than a percentage that is two standard deviations below the reference mean percentage indicates infertile. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal male fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

Another embodiment disclosed herein is a method for determining male fertility status. In one embodiment, the method includes exposing a first portion of a sperm sample from a male to non-capacitating conditions to obtain an in vitro non-capacitated sperm sample; exposing a second portion of the sperm sample to capacitating conditions to obtain an in vitro capacitated sperm sample; fixing the in vitro non-capacitated sperm sample and the in vitro capacitated sperm sample with a fixative for a time period of at least: one hour, two hours, four hours, eight hours, twelve hours, eighteen hours or twenty four hours; treating the fixed in vitro non-capacitated sperm sample and the fixed in vitro capacitated sperm sample with a labeling molecule for $G_{M1}$ localization patterns, wherein the labeling molecule has a detectable label; identifying more than one labeled $G_{M1}$ localization patterns for the labeled fixed in vitro non-capacitated sperm sample and the labeled fixed in vitro capacitated sperm sample, said $G_{M1}$ labeled localization patterns being an apical acrosome (AA) $G_{M1}$ localization pattern, an acrosomal plasma membrane (APM) $G_{M1}$ localization pattern, a Lined-Cell $G_{M1}$ localization pattern and all other labeled $G_{M1}$ localization patterns; comparing the labeled $G_{M1}$ localization patterns for the labeled fixed in vitro non-capacitated sperm sample to the labeled $G_{M1}$ localization patterns for the labeled fixed in vitro capacitated sperm sample; based on the comparison, assigning the apical acrosome (AA) $G_{M1}$ localization pattern and the acrosomal plasma membrane (APM) $G_{M1}$ localization pattern to a capacitated state and assigning the Lined-Cell $G_{M1}$ localization pattern and all other labeled $G_{M1}$ localization patterns to a non-capacitated state; and characterizing a fertility status of the male based on the identified $G_{M1}$ labeled localization patterns for the labeled fixed in vitro non-capacitated sperm sample and the labeled fixed in vitro capacitated sperm sample. In one embodiment, the characterizing step comprises the steps of: determining a fertility threshold associated with a percentage of [(AA $G_{M1}$ localization patterns plus APM $G_{M1}$ localization patterns)/total $G_{M1}$ localization patterns] for the labeled fixed in vitro capacitated sperm sample; wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates fertile; less than a percentage that is one standard deviation below the reference mean percentage and greater than a percentage that is two standard deviations below the reference mean percentage indicates sub-fertile; greater than two standard deviations below the reference mean percentage indicates infertile. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal male fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In one embodiment, prior to the exposing steps, a semen sample is treated to decrease semen viscosity using a wide orifice pipette made of non-metallic material and using a reagent that does not damage sperm membranes chosen from the various reagents that are used to decrease semen viscosity. In some such embodiments, the membrane damaging reagents potentially may include (i) a protease; (ii) a nuclease (iii) a mucolytic agent; (iv) a lipase; (v) an esterase and (vi) glycoside hydrolases. In some embodiments, the identifying step is repeated until the number of Lined-Cell $G_{M1}$ localization patterns is substantially constant. In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, the number of Lined-Cell $G_{M1}$ localization patterns, for the labeled fixed in vitro non-capacitated sperm is determined until the number is less than: 25%, 20%, 15% or 10% of the total number of labeled cells; or ranges from 2% to 25%; 2% to 20%; 2 to 15%; 2 to 10%; 2 to 5% of the total number of labeled cells. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

In another such embodiment, the characterizing step further includes the steps of: determining the number of each $G_{M1}$ labeled localization patterns for a predetermined number of the labeled fixed in vitro non-capacitated sperm sample; determining the number of each $G_{M1}$ labeled localization patterns for a predetermined number of the labeled fixed in vitro capacitated sperm sample; calculating a ratio for a sum of the number of AA $G_{M1}$ localization patterns and number of APM $G_{M1}$ localization patterns over a sum of the total number of $G_{M1}$ labeled localization patterns for the labeled fixed in vitro non-capacitated sperm sample; and calculating a ratio for a sum of the number of AA $G_{M1}$ localization patterns and number of APM $G_{M1}$ localization patterns over a sum of the total number of $G_{M1}$ labeled localization patterns for the labeled fixed in vitro capacitated sperm sample.

In one embodiment disclosed herein the method further includes the steps of: comparing the ratio for the labeled fixed in vitro non-capacitated sperm to a ratio of labeled fixed in vitro non-capacitated sperm having a known fertility status; and comparing the ratio for the labeled fixed in vitro capacitated sperm to a ratio of labeled fixed in vitro capacitated sperm having a known fertility status.

Yet another embodiment disclosed herein is a method for determining male fertility status. In one embodiment, the method includes the steps of: obtaining a first portion of a sperm sample from a male that has been exposed to in vitro non-capacitating conditions, fixed in a fixative for at least: one hour, two hours, four hours, eight hours, twelve hours, eighteen hours or twenty four hours, and treated with a labeling molecule for $G_{M1}$ localization patterns, wherein the labeling molecule has a detectable label; obtaining a second portion of the sperm sample that has been exposed to in vitro capacitating conditions, fixed in a fixative, and treated with the labeling molecule for $G_{M1}$ localization patterns; identifying more than one $G_{M1}$ labeled localization patterns for the labeled fixed in vitro non-capacitated sperm sample and the labeled fixed in vitro capacitated sperm sample, said $G_{M1}$ labeled localization patterns being an apical acrosome (AA) $G_{M1}$ localization pattern, an acrosomal plasma membrane (APM) $G_{M1}$ localization pattern, a Lined-Cell $G_{M1}$ localization pattern and all other labeled $G_{M1}$ localization patterns; comparing the labeled $G_{M1}$ localization patterns for the labeled fixed in vitro non-capacitated sperm sample to the labeled $G_{M1}$ localization patterns for the labeled fixed in vitro capacitated sperm sample; based on the comparison, assigning the apical acrosome (AA) $G_{M1}$ localization pattern and the acrosomal plasma membrane (APM) $G_{M1}$ localization pattern to a capacitated state and assigning the Lined-Cell $G_{M1}$ localization pattern and all other labeled $G_{M1}$ localization patterns to a non-capacitated state; and characterizing a fertility status of the male based on the identified $G_{M1}$ labeled localization patterns for the labeled fixed in vitro non-capacitated sperm sample and the labeled fixed in vitro capacitated sperm sample. In one such embodiment, the characterizing step comprises the steps of: determining a fertility threshold associated with a percentage of [(AA $G_{M1}$ localization patterns plus APM $G_{M1}$ localization patterns)/total $G_{M1}$ localization patterns] for the labeled fixed in vitro capacitated sperm sample; wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates fertile; less than a percentage that is one standard deviation below the reference mean percentage and greater than a percentage that is two standard deviations below the reference mean percentage indicates sub-fertile; less than a percentage that is two standard deviations below the reference mean percentage indicates infertile; comparing the percentage of [(AA $G_{M1}$ localization patterns plus APM $G_{M1}$ localization patterns)/total $G_{M1}$ localization patterns] for the labeled fixed in vitro capacitated sperm sample to the reference percentage of [(AA $G_{M1}$ localization patterns plus APM $G_{M1}$ localization patterns)/total $G_{M1}$ localization patterns] and identifying the fertility threshold based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In some embodiments, the identifying step is repeated until the number of Lined-Cell $G_{M1}$ localization patterns is substantially constant. In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, determining the number of Lined-Cell $G_{M1}$ localization patterns, for the labeled fixed in vitro non-capacitated sperm until the number is less than: 25%, 20%, 15% or 10% of the total number of labeled cells; or ranges from 2% to 25%; 2% to 20%; 2 to 15%; 2 to 10%; 2 to 5% of the total number of labeled cells.

In one embodiment of such method, the method further includes the steps of: determining the number of each $G_{M1}$ labeled localization patterns for a predetermined number of the labeled fixed in vitro non-capacitated sperm sample and the labeled fixed in vitro capacitated sperm sample, and calculating a ratio for a sum of the number of AA $G_{M1}$ localization patterns and number of APM $G_{M1}$ localization patterns over a sum of the total number of $G_{M1}$ localization patterns each for the labeled fixed in vitro non-capacitated sperm sample and the labeled fixed in vitro capacitated sperm sample.

In another embodiment, the characterizing step further includes the steps of: comparing the ratio for the labeled fixed in vitro capacitated sperm sample to ratios of $G_{M1}$ localization patterns of in vitro capacitated sperm for males having a known fertility status; and comparing the ratio for the labeled fixed in vitro non-capacitated sperm sample to ratios of $G_{M1}$ localization patterns in vitro non-capacitated sperm for males having a known fertility status.

Still yet another embodiment disclosed herein is a method for determining male fertility status. In one embodiment, the method includes the steps of: exposing, in vitro, a sperm sample from a male to capacitating conditions; fixing the capacitated sperm sample with a fixative for at least: one hour, two hours, four hours, eight hours, twelve hours, eighteen hours or twenty four hours; treating the fixed in vitro capacitated sperm sample with a labeling molecule for $G_{M1}$ localization patterns, wherein the labeling molecule has a detectable label; identifying more than one $G_{M1}$ labeled localization patterns for the labeled fixed in vitro capacitated sperm sample, said $G_{M1}$ labeled localization patterns being an apical acrosome (AA) $G_{M1}$ localization pattern, an acrosomal plasma membrane (APM) $G_{M1}$ localization pattern, a Lined-Cell $G_{M1}$ localization pattern and all other labeled $G_{M1}$ localization patterns; assigning the apical acrosome (AA) $G_{M1}$ localization pattern and the acrosomal plasma membrane (APM) $G_{M1}$ localization pattern to a capacitated state and assigning the Lined-Cell $G_{M1}$ localization pattern and all other labeled $G_{M1}$ localization patterns to a non-capacitated state; and characterizing a fertility status of the male. In one embodiment, the characterizing step comprises the steps of: determining a fertility threshold associated with a percentage of [(AA $G_{M1}$ localization patterns plus APM $G_{M1}$ localization patterns)/total $G_{M1}$ localization patterns] for the labeled fixed in vitro capacitated sperm sample; wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates fertile; less than a percentage that is one standard deviation below the reference mean percentage and greater than a percentage that is two standard deviations below the reference mean percentage indicates sub-fertile; less than two standard deviations below the reference mean percentage indicates infertile; comparing the percentage of [(AA $G_{M1}$ localization patterns plus APM $G_{M1}$ localization patterns)/total $G_{M1}$ localization patterns] for the labeled fixed in vitro capacitated sperm sample to the reference percentage of [(AA $G_{M1}$ localization patterns plus APM $G_{M1}$ localization patterns)/ total $G_{M1}$ localization patterns] and identifying the fertility threshold based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal male fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In one embodiment, prior to the exposing steps, a semen sample is treated to decrease semen viscosity using a wide orifice pipette made of non-metallic material and using a reagent that does not damage sperm membrane chosen from the various reagents that are used to decrease semen viscosity. In some embodiments, the membrane damaging reagent may be potentially selected from the group consisting of (i) a protease; (ii) a nuclease (iii) a mucolytic agent; (iv) a lipase; (v) an esterase and (vi) glycoside hydrolases. In some embodiments, the identifying step is repeated until the number of Lined-Cell $G_{M1}$ localization patterns is substantially constant. In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, determining the number of Lined-Cell $G_{M1}$ localization patterns, for the labeled fixed in vitro non-capacitated sperm until the number is less than: 25%, 20%, 15% or 10% of the total number of labeled cells; or ranges from 2% to 25%; 2% to 20%; 2 to 15%; 2 to 10%; 2 to 5% of the total number of labeled cells. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

In one embodiment of such method, the method further includes the steps of: comparing the ratio of $G_{M1}$ localization patterns to ratios of $G_{M1}$ localization patterns for males having a known fertility status. In one such embodiment, the comparing step includes the steps of: determining the number of each $G_{M1}$ labeled localization patterns for a predetermined number of the labeled fixed in vitro capacitated sperm sample, and calculating a ratio for a sum of the number of AA $G_{M1}$ localization patterns and number of APM $G_{M1}$ localization patterns over a sum of the total number of $G_{M1}$ labeled localization patterns.

Another embodiment disclosed herein is a method for determining male fertility status. In one embodiment, the method includes the steps of: obtaining a first portion of a sperm sample from a male that has been exposed to in vitro capacitating conditions, fixed in a fixative for at least: one hour, two hours, four hours, eight hours, twelve hours, eighteen hours or twenty four hours, and stained with a labeling molecule for $G_{M1}$ localization patterns, wherein the labeling molecule has a detectable label; identifying more than one $G_{M1}$ labeled localization patterns for the labeled fixed in vitro capacitated sperm sample, said $G_{M1}$ localization patterns being an apical acrosome (AA) $G_{M1}$ localization pattern, an acrosomal plasma membrane (APM) $G_{M1}$ localization pattern, a Lined-Cell $G_{M1}$ localization pattern and all other labeled $G_{M1}$ localization patterns; assigning the apical acrosome (AA) $G_{M1}$ localization pattern and the acrosomal plasma membrane (APM) $G_{M1}$ localization pattern to a capacitated state and assigning the Lined-Cell $G_{M1}$ localization pattern and all other labeled $G_{M1}$ localization patterns to a non-capacitated state; and characterizing a fertility status of the male. In some embodiments, characterizing step comprises the steps of: determining a fertility threshold associated with a percentage of [(AA $G_{M1}$ localization patterns plus APM $G_{M1}$ localization patterns)/total $G_{M1}$ localization patterns] for the labeled fixed in vitro capacitated sperm sample; wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates fertile; less than a percentage that is one standard deviation below the reference mean percentage and greater than a percentage that is two standard deviations below the reference mean percentage indicates sub-fertile; less than a percentage that is two standard deviations below the reference mean percentage indicates infertile; comparing the percentage of [(AA $G_{M1}$ localization patterns plus APM $G_{M1}$ localization patterns)/total $G_{M1}$ localization patterns] for the labeled fixed in vitro capacitated sperm sample to the reference percentage of [(AA $G_{M1}$ localization patterns plus APM $G_{M1}$ localization patterns)/total $G_{M1}$ localization patterns] and identifying the fertility threshold based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal male fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In some embodiments, the identifying step is repeated until the number of Lined-Cell $G_{M1}$ localization patterns is substantially constant. In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, determining the number of Lined-Cell $G_{M1}$ localization patterns, for the labeled fixed in vitro non-capacitated sperm until the number is less than: 25%, 20%, 15% or 10% of the total number of labeled cells; or ranges from 2% to 25%; 2% to 20%; 2 to 15%; 2 to 10%; 2 to 5% of the total number of labeled cells.

In one embodiment of such method, the method further includes the steps of: comparing the ratio of $G_{M1}$ localization patterns to ratios of $G_{M1}$ localization patterns for males having a known fertility status. In one such embodiment, the comparing step includes the steps of: determining the number of each $G_{M1}$ labeled localization patterns for a predetermined number of the labeled fixed in vitro capacitated sperm sample, and calculating a ratio for a sum of the number of AA $G_{M1}$ localization patterns and number of APM $G_{M1}$ localization patterns over a sum of the total number of $G_{M1}$ labeled localization patterns.

Another embodiment disclosed herein is a method for determining male fertility status. In one embodiment, the method includes the steps of: obtaining a sperm sample, wherein at least a portion of the sperm sample has been exposed to in vitro capacitating conditions to obtain in vitro capacitated sperm, has been exposed to a fixative for at least: one hour, two hours, four hours, eight hours, twelve hours, eighteen hours or twenty four hours, and has been stained for $G_{M1}$; obtaining values for one or more semen parameters of the sperm sample; determining a Cap-Score of the labeled fixed in vitro capacitated sperm sample based on one or more $G_{M1}$ labeled localization patterns, said $G_{M1}$ labeled localization patterns being an apical acrosome (AA) $G_{M1}$ localization pattern, a post-acrosomal plasma membrane (APM) $G_{M1}$ localization pattern, a Lined-Cell $G_{M1}$ localization pattern and all other labeled $G_{M1}$ localization patterns; and calculating a male fertility index (MFI) value of the male based on the determined CAP score and the one or more obtained semen parameters. In one embodiment, the one or more semen parameters of the sperm sample are selected from the group consisting of volume of the original sperm sample, concentration of sperm, motility of sperm, and morphology of sperm. In some embodiments, the identifying step is repeated until the number of Lined-Cell $G_{M1}$ localization patterns is substantially constant.

In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, determining the number of Lined-Cell $G_{M1}$ localization patterns, for the labeled fixed in vitro non-capacitated sperm until the number is less than: 25%, 20%, 15% or 10% of the total number of labeled cells; or ranges from 2% to 25%; 2% to 20%; 2 to 15%; 2 to 10%; 2 to 5% of the total number of labeled cells.

In various embodiments of the methods described herein, the more than one of $G_{M1}$ labeled localization patterns comprises AA $G_{M1}$ localization pattern, APM $G_{M1}$ localization pattern, Lined-Cell $G_{M1}$ localization pattern, intermediate (INTER) $G_{M1}$ localization pattern, post acrosomal plasma membrane (PAPM) $G_{M1}$ localization pattern, apical acrosome/post acrosome (AA/PA) $G_{M1}$ localization pattern, equatorial segment (ES) $G_{M1}$ localization pattern, and diffuse (DIFF) $G_{M1}$ localization pattern.

In one embodiment, exposing the first portion of the sperm sample to non-capacitating conditions and exposing the second portion of the sperm sample to capacitating conditions occur concurrently.

In one embodiment disclosed herein is a kit for identifying a fertility status of a male comprising: a diagram illustrating one or more $G_{M1}$ localization patterns of capacitated sperm and one of more $G_{M1}$ localization patterns of non-capacitated sperm, wherein said $G_{M1}$ localization patterns of capacitated sperm and $G_{M1}$ localization patterns of non-capacitated sperm are reflective of known fertility status; a wide orifice pipette having an orifice of sufficient size in diameter to prevent shearing of a sperm membrane; one or more of the following: capacitating media, non-capacitating media, fixative composition, labeling reagents for determining $G_{M1}$ localization patterns; with the proviso that the fixative composition does not damage sperm membranes, wherein the capacitating media and non-capacitating media, when applied in vitro to sperm cells, produce $G_{M1}$ localization patterns indicative of capacitated sperm and patterns indicative of non-capacitated sperm as reflected in the diagram. In one embodiment, the kit contains instructions for handling sperm in order to avoid damaging the sperm membrane. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

In certain embodiments described herein, the in vitro capacitating conditions include exposure to one or more bicarbonate ions, calcium ions, and a mediator of sterol efflux. In some embodiments, the mediator of sterol efflux is 2-hydroxy-propyl-β-cyclodextrin, methyl-β-cyclodextrin, serum albumin, high density lipoprotein, phospholipid vesicles, fetal cord serum ultrafiltrate, fatty acid binding proteins, or liposomes. In one embodiment, the mediator of sterol efflux is 2-hydroxy-propyl-β-cyclodextrin.

In one embodiment, the non-capacitating conditions include the lack of exposure to one or more of bicarbonate ions, calcium ions, and a mediator of sterol efflux.

In certain embodiments described herein, the fixative is an aldehyde fixative. In one embodiment, the fixative includes paraformaldehyde, glutaraldehyde or combinations thereof. In certain embodiments, the affinity molecule for $G_{M1}$ is fluorescent labeled cholera toxin b subunit.

BRIEF DESCRIPTION OF THE DRAWINGS

The foregoing summary, as well as the following detailed description of embodiments of the methods and kits for determining male fertility status, will be better understood when read in conjunction with the appended drawings. It should be understood, however, that the invention is not limited to the precise arrangements and instrumentalities shown.

In the drawings.

DETAILED DESCRIPTION OF THE DISCLOSURE

Figure 1:
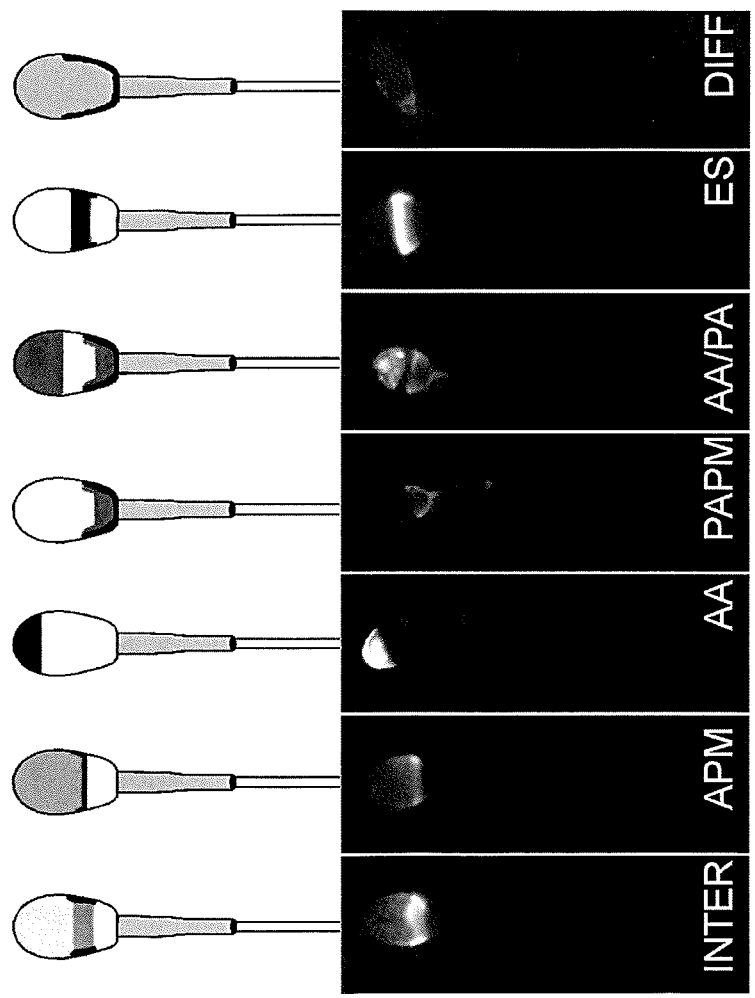
FIG. 1 shows INTER, APM, AA, PAPM, AA/PA, ES, and DIFF localization patterns of $G_{M1}$ in normal human sperm and sperm from infertile males under non-capacitating conditions or capacitating conditions.

With reference to the accompanying drawings, various embodiments of the present invention are described more fully below. Some but not all embodiments of the present invention are shown. Indeed, various embodiments of the invention may be embodied in many different forms and should not be construed as limited to the embodiments expressly described. It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Each and every reference identified herein is incorporated by reference in its entirety.

Unless specifically set forth herein, the terms "a", "an" and "the" are not limited to one element but instead should be read as meaning "at least one".

"About" is understood to mean the range of + and −10% of the value referenced. However, use of "about" in reference to a value does not exclude the possibility of the referenced value alone. For example, "about 1 hour" is understood to fully support "54 minutes," "1 hour," and "66 minutes."

The present disclosure is based on the observations that certain $G_{M1}$ localization patterns can provide information regarding male fertility status. Determination of $G_{M1}$ localization patterns is described in U.S. Pat. Nos. 7,160,676, 7,670,763, and 8,367,313, the disclosures of which are incorporated herein by reference. This disclosure provides methods and kits for determination of male fertility status. In certain embodiments, the method is based on a change in the percentage of certain $G_{M1}$ localization patterns upon exposure to in vitro capacitating stimuli. In other embodiments, the method is based specifically on a change in the percentage of a Lined-Cell $G_{M1}$ localization pattern upon exposure to in vitro capacitating stimuli.

In one embodiment, disclosed herein is a method for determining male fertility status. In one embodiment, the method includes subjecting a sperm sample from an individual to in vitro capacitating and in vitro non-capacitating conditions, determining a change in the percentage of certain $G_{M1}$ localization patterns upon exposure to in vitro capacitating conditions, and based on the level of change, identifying the fertility status.

The term "in vitro capacitated" sperm refers to sperm which have been incubated under conditions which promote the process of capacitation. In one embodiment, capacitation conditions include the presence in the medium of one or more of bicarbonate ions, calcium ions, and a sterol acceptor, e.g., serum albumin or a cyclodextrin. In one embodiment, in vitro capacitation conditions include the presence of bicarbonate and calcium ions in the medium, and the presence of a sterol acceptor. In one embodiment, a sterol acceptor is a mediator of sterol efflux. Capacitated sperm have acquired the ability to undergo acrosome exocytosis and have acquired a hyperactivated pattern of motility. The term "in vitro non-capacitated" sperm refers to sperm which are not incubated with one or more of the above-listed stimuli for capacitation. In one embodiment, non-capacitation conditions include the absence of capacitation conditions. In another embodiment, non-capacitation conditions include the absence of one or more of the stimuli needed for capacitation. Non-capacitated sperm do not undergo acrosome exocytosis induced by a physiological ligand such as the zona pellucida, solubilized proteins from the zona pellucida, or progesterone. In addition, sperm incubated under non-capacitating conditions also will not demonstrate hyperactivated motility.

In one embodiment, capacitation may be induced in vitro by exposure to external stimuli such as bicarbonate and calcium ions, and mediators of sterol efflux, e.g., 2-hydroxypropyl-β-cyclodextrin, methyl-β-cyclodextrin, serum albumin, high density lipoprotein, phospholipids vesicles, liposomes, etc. In certain embodiments, an identifiable change in the $G_{M1}$ localization pattern is observed when sperm are exposed to one or more of these stimuli in vitro.

In one embodiment, after collection, semen samples are typically processed in some way, including one or more of the following: liquefaction, washing, and/or enrichment. In some embodiments, liquefaction involves allowing the sample to liquefy at room temperature or at 37° C. (or any temperature there between) for various time periods (typically 15-20 minutes, but ranging from 10-60 minutes). Liquefaction is a process through which the seminal plasma converts from a gel into a more fluid/liquid consistency. Seminal plasma will typically liquefy without any manipulation, but with especially viscous samples, or if there is a desire to hasten the process or make a consistent liquefaction protocol by which all samples are handled, individuals might manipulate the sample to achieve liquefaction. In certain embodiments the semen sample is manipulated to decrease semen viscosity by using a wide orifice pipette made of non-metallic material. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm. In certain embodiments, one can also achieve liquefaction by adding various reagents which do not damage sperm membrane. Reagents which should be avoided are those that damage sperm membrane. The sperm can be washed by centrifugation and resuspension and subjected to semen analysis, and/or be subjected to one or more selection processes including: layering on top of, and centrifugation through a density gradient; layering on top of, and centrifugation through a density gradient followed by collection of the sperm-enriched fraction followed by resuspension and washing; layering on top of, and centrifugation through a density gradient followed by collection of the sperm-enriched fraction and overlaying on top of that a less dense medium into which motile sperm will swim up; or overlaying a less dense medium on top of the sample and allowing motile sperm to swim up into it.

After initial processing, the sperm can be counted, and a given number of sperm can then be placed into containers (such as tubes) containing in vitro non-capacitating or in vitro capacitating medium to achieve desired final concentrations. In one embodiment, the final typical concentration of sperm is 1,000,000/ml (final concentration ranges might vary from 250,000/ml-250,000,000/ml).

The base medium for incubating the sperm under in vitro non-capacitating and capacitating in vitro conditions can be a physiological buffered solution such as, but not limited to, human tubal fluid (HTF); modified human tubal fluid (mHTF); Whitten's medium; modified Whitten's medium; KSOM; phosphate-buffered saline; HEPES-buffered saline; Tris-buffered saline; Ham's F-10; Tyrode's medium; modified Tyrode's medium; TES-Tris (TEST)-yolk buffer; or Biggers, Whitten and Whittingham (BWW) medium. The base medium can have one or more defined or complex sources of protein and other factors added to it, including fetal cord serum ultrafiltrate, Plasmanate, egg yolk, skim milk, albumin, lipoproteins, or fatty acid binding proteins, either to promote viability or at concentrations sufficient to help induce capacitation. Typical stimuli for capacitation include one or more of the following: bicarbonate (typically at 20-25 mM, with ranges from 5-50 mM), calcium (typically at 1-2 mM, with ranges from 0.1-10 mM), and/or cyclodextrin (typically at 1-3 mM, with ranges from 0.1-20 mM). Cyclodextrins may comprise 2-hydroxy-propyl-β-cyclodextrin and/or methyl-β-cyclodextrin. Incubation temperatures are typically 37° C. (ranging from 30° C.–38° C.), and incubation times are typically 1-4 hours (ranging from 30 minutes to 18 hours), though baseline samples can be taken at the start of the incubation period ("time zero").

In one embodiment, for generating patterns of $G_{M1}$, the sperm are washed with a standard base medium (e.g., phosphate-buffered saline, Modified Whitten's medium, or other similar media) and incubated with a labeling molecule for $G_{M1}$ which has a detectable label on it. Since $G_{M1}$ has extracellular sugar residues which can serve as an epitope, it can be visualized without having to fix and permeabilize the cells. However, fixation of the cells results in better preservation of the specimen, easier visualization (compared to discerning patterns in swimming sperm) and allows longer visualization time, while contributing to pattern formation. Various fixatives known for histological study of spermatozoa are within the purview of those skilled in the art. Suitable fixatives include paraformaldehyde, glutaraldehyde, Bouin's fixative, and fixatives comprising sodium cacodylate, calcium chloride, picric acid, tannic acid and like. In one embodiment, paraformaldehyde, glutaraldehyde or combinations thereof are used.

Fixation conditions can range from about 0.004% (weight/volume) paraformaldehyde to about 4% (weight/volume) paraformaldehyde, although about 0.01% to about 1% (weight/volume) paraformaldehyde is typically used. In one embodiment, about 0.005% (weight/volume) paraformaldehyde to about 1% (weight/volume) paraformaldehyde can be used. In one embodiment, about 4% paraformaldehyde (weight/volume), about 0.1% glutaraldehyde (weight/volume) and about 5 mM $CaCl_2$ in phosphate buffered saline can be used.

The period of time a sperm sample is fixed in a fixative may vary. In one embodiment, a sperm sample is fixed in fixative for about 5 hours or less. In one embodiment, a sperm sample is fixed in a fixative for greater than about 5 hours. In another embodiment, a sperm sample is fixed in a fixative for about 0.5 hours, for about 1 hours, for about 1.5 hours, for about 2 hours, for about 2.5 hours, for about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, about 24 hours, about 24.5 hours, about 25 hours, about 25.5 hours, about 26 hours, about 26.5 hours, about 27 hours, about 27.5 hours, about 28 hours, about 28.5 hours, about 29 hours, about 29.5 hours, about 30, or any range determinable from the preceding times (for example, about 26 hours to about 28 hours, or about 3 hours to about 5 hours).

The localization pattern of $G_{M1}$ in live or fixed sperm can be obtained by using labeling binding techniques. A molecule having specific affinity for the $G_{M1}$ ganglioside can be used. The labeling molecule can be directly linked to a detectable label (such as a fluorophore) or may be detected by a second labeling molecule which has a detectable label on it. For example, the b subunit of cholera toxin is known to specifically bind to $G_{M1}$. Therefore, a labeled (such as fluorescent labeled) cholera toxin b subunit can be used to obtain a pattern of distribution of $G_{M1}$. In one embodiment, final concentrations of the b subunit of cholera toxin linked to fluorophore are about 10 µg/ml to about 15 µg/ml. In another embodiment, the final concentrations of the b subunit of cholera toxin linked to fluorophore are about 0.1 µg/ml to about 50 µg/ml. Alternatively, a labeled antibody to $G_{M1}$ can be used. In yet another alternative, a labeled antibody to the cholera toxin b subunit can be used to visualize the pattern of $G_{M1}$ staining. And in yet another alternative, a labeled secondary antibody which binds to either the primary antibody that binds directly to $G_{M1}$ or to the primary antibody that binds to the b subunit of cholera toxin could be used. The term "$G_{M1}$ staining" or "staining of $G_{M1}$" or "labeling" or related terms as used herein means the staining seen on or in cells due to the binding of labeled affinity molecules to $G_{M1}$. For example, when fluorescent tagged/labeled cholera toxin b subunit is used for localization of $G_{M1}$, the signal or staining is from the cholera toxin b subunit but is indicative of the location of $G_{M1}$. The terms "signal" and "staining" and "labeling" are used interchangeably. The detectable label is such that it is capable of producing a detectable signal. Such labels include a radionuclide, an enzyme, a fluorescent agent or a chromophore. Labeling (or staining) and visualization of $G_{M1}$ distribution in sperm is carried out by standard techniques. Labeling molecules other than the b subunit of cholera toxin can also be used. These include polyclonal and monoclonal antibodies. Specific antibodies to $G_{M1}$ ganglioside can be generated by routine immunization protocols, or can be purchased commercially (e.g., Matreya, Inc., State College, PA). The antibodies may be raised against $G_{M1}$ or, can be generated by using peptide mimics of relevant epitopes of the $G_{M1}$ molecule. Identification and generation of peptide mimics is well known to those skilled in the art. In addition, the binding of the b subunit to cholera toxin might be mimicked by a small molecule. Identification of small molecules that have similar binding properties to a given reagent is well known to those skilled in the art.

For human sperm, eight different localization patterns (see details under Example 1) were observed when the sperm was under in vitro capacitating conditions. These patterns are designated as INTER, APM, AA, PAPM, AA/PA, ES, DIFF, and Lined Cell. The INTER, APM, AA, PAPM, AA/PA, ES, and DIFF patterns are shown in FIG. 1 and the Lined-Cell pattern is shown in FIGS. 6A, 6B, 6C, and 6D, each of which are further described below:

INTER: The vast majority of the fluorescence is in a band around the equatorial segment, with some signal in the plasma membrane overlying the acrosome. There is usually a gradient of signal, with the most at the equatorial segment and then progressively less toward the tip. There is often an increase in signal intensity on the edges of the sperm head in the band across the equatorial segment.

APM (Acrosomal Plasma Membrane): Compared to INTER there is less distinction in this pattern between the equatorial signal and that moving toward the apical tip. That is, the signal in the plasma membrane overlying the acrosome is more evenly distributed. APM signal is seen either from the bright equatorial INTER band moving apically toward the tip, or it can start further up toward the tip and be found in a smaller region, as it is a continuum with the AA.

AA (Apical Acrosome): In this pattern, the fluorescence is becoming more and more concentrated toward the apical tip, increased in brightness and reduced in area with signal.

PAPM (Post Acrosomal Plasma Membrane): Signal is exclusively in the post-acrosomal plasma membrane.

AA/PA (Apical Acrosome/Post Acrosome): Signal is both in the plasma membrane overlying the acrosome and post-acrosomal plasma membrane. Signal is missing from the equatorial segment.

ES (Equatorial Segment): Bright signal is seen solely in the equatorial segment. It may be accompanied by thickening of the sperm head across the equatorial region.

DIFF (Diffuse): Diffuse signal is seen over the whole sperm head.

Lined-Cell: Signal is seen at the top of the post-acrosomal region and at the plasma membrane overlying the acrosome as well as the bottom of the equatorial segment (i.e., the post acrosome/equatorial band). Signal is missing around the equatorial segment.

The term "$G_{M1}$ localization pattern" is used interchangeably with "pattern" or "localization pattern."

Figure 6B:
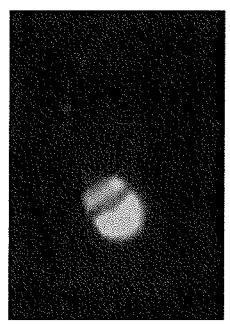
FIGS. 6A, 6B, 6C, and 6D show Lined-Cell $G_{M1}$ localization patterns of $G_{M1}$ in sperm from infertile males under capacitating conditions.
Figure 6D:
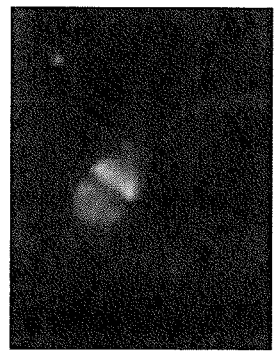
Figure 6A:
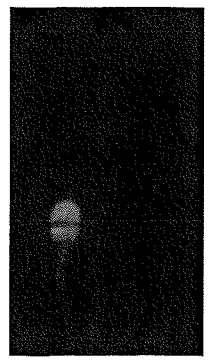
Figure 6C:
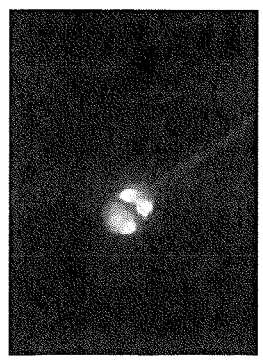

FIGS. 6A, 6B, 6C, and 6D show Lined-Cell $G_{M1}$ localization patterns of $G_{M1}$ in sperm from infertile males under capacitating conditions. Specifically, FIG. 6A shows a Lined-Cell $G_{M1}$ localization pattern where the signal is evenly distributed at the post acrosome/equatorial band and at the plasma membrane overlying the acrosome. FIG. 6B shows a Lined-Cell $G_{M1}$ localization pattern where the signal at the plasma membrane overlying the acrosome is brighter than the signal at the post acrosome/equatorial band. FIGS. 6C and 6D show a signal at the post acrosome/ equatorial band that is brighter than the signal at the plasma membrane overlying the acrosome.

It was observed that while the INTER, AA, APM patterns, and combinations of these patterns, correlate positively with viable sperm with normal sperm membrane architecture and therefore fertility, the PAPM, AA/PA, ES, DIFF, and the Lined-Cell patterns do not positively correlate with viability, normal membrane architecture and fertility. If incubated under non-capacitating conditions, the majority of viable sperm with normal membrane architecture will exhibit the INTER pattern, which is characterized by the majority of labeling being near the equatorial segment, with the rest extending through the plasma membrane overlying the acrosome. Additionally, there is an increase in the number of the APM and AA patterns upon exposure to stimuli for capacitation. The APM pattern shows more uniform signal in the plasma membrane overlying the acrosome, whereas the AA pattern shows increasing intensity of signal in the rostral part of the sperm head, the apical acrosome, and reduced signal moving caudally toward the equatorial segment. Sperm incubated under in vitro non-capacitated conditions for infertile individuals have $G_{M1}$ localization patterns that are similar to $G_{M1}$ localization patterns of sperm incubated under in vitro non-capacitated conditions for normal individuals.

In one embodiment disclosed herein is a method for determining male fertility status. In one embodiment, the method includes the steps of exposing a first portion of a sperm sample from a male to non-capacitating conditions to obtain an in vitro non-capacitated sperm sample; exposing a second portion of the sperm sample to capacitating conditions to obtain an in vitro capacitated sperm sample; fixing the in vitro non-capacitated sperm sample and the in vitro capacitated sperm sample with a fixative for a time period of at least: one hour, two hours, four hours, eight hours, twelve hours, eighteen hours or twenty four hours, treating the fixed in vitro non-capacitated sperm sample and the fixed in vitro capacitated sperm sample with a labeling molecule for $G_{M1}$ localization patterns, wherein the labeling molecule has a detectable label; identifying more than one labeled $G_{M1}$ localization patterns for the labeled fixed in vitro non-capacitated sperm sample and the labeled fixed in vitro capacitated sperm sample, said $G_{M1}$ labeled localization patterns being an apical acrosome (AA) $G_{M1}$ localization pattern, an acrosomal plasma membrane (APM) $G_{M1}$ localization pattern, a Lined-Cell $G_{M1}$ localization pattern and all other labeled $G_{M1}$ localization patterns; comparing the labeled $G_{M1}$ localization patterns for the labeled fixed in vitro non-capacitated sperm sample to the labeled $G_{M1}$ localization patterns for the labeled fixed in vitro capacitated sperm sample; based on the comparison, assigning the apical acrosome (AA) $G_{M1}$ localization pattern and the acrosomal plasma membrane (APM) $G_{M1}$ localization pattern to a capacitated state and assigning the Lined-Cell $G_{M1}$ localization pattern and all other labeled $G_{M1}$ localization patterns to a non-capacitated state; and characterizing a fertility status of the male based on the identified $G_{M1}$ labeled localization patterns for the labeled fixed in vitro non-capacitated sperm sample and the labeled fixed in vitro capacitated sperm sample. In one embodiment, the characterizing step comprises the steps of: determining a fertility threshold associated with a percentage of [(AA $G_{M1}$ localization patterns plus APM $G_{M1}$ localization patterns)/total $G_{M1}$ localization patterns] for the labeled fixed in vitro capacitated sperm sample; wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates fertile; less than a percentage that is one standard deviation below the reference mean percentage and greater than a percentage that is two standard deviations below the reference mean percentage indicates sub-fertile; less than a percentage that is two standard deviations below the reference mean percentage indicates infertile; comparing the percentage of [(AA $G_{M1}$ localization patterns plus APM $G_{M1}$ localization patterns)/total $G_{M1}$ localization patterns] for the labeled fixed in vitro capacitated sperm sample to the reference percentage of [(AA $G_{M1}$ localization patterns plus APM $G_{M1}$ localization patterns)/total $G_{M1}$ localization patterns] and identifying the fertility threshold based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal male fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In one embodiment, prior to the exposing steps, a semen sample is treated to decrease semen viscosity using a wide orifice pipette made of non-metallic material and using a reagent that does not damage sperm membrane chosen from the various reagents that are used to decrease semen viscosity. In some embodiments, the membrane damaging reagent is selected from the group consisting of (i) a protease; (ii) a nuclease (iii) a mucolytic agent; (iv) a lipase; (v) an esterase and (vi) glycoside hydrolases. In some embodiments, the identifying step is repeated until the number of Lined-Cell $G_{M1}$ localization patterns is substantially constant. In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, determining the number of Lined-Cell $G_{M1}$ localization patterns, for the labeled fixed in vitro non-capacitated sperm until the number is less than: 25%, 20%, 15% or 10% of the total number of labeled cells; or ranges from 2% to 25%; 2% to 20%; 2 to 15%; 2 to 10%; 2 to 5% of the total number of labeled cells. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

In one such embodiment, the characterizing step may include the steps of: determining the number of each $G_{M1}$ labeled localization patterns for a predetermined number of the labeled fixed in vitro non-capacitated sperm sample; determining the number of each $G_{M1}$ labeled localization patterns for a predetermined number of the labeled fixed in vitro capacitated sperm sample; calculating a ratio for a sum of the number of AA $G_{M1}$ localization patterns and number of APM $G_{M1}$ localization patterns over a sum of the total number of $G_{M1}$ labeled localization patterns for the labeled fixed in vitro non-capacitated sperm sample; and calculating a ratio for a sum of the number of AA $G_{M1}$ localization patterns and number of APM $G_{M1}$ localization patterns over a sum of the total number of $G_{M1}$ labeled localization patterns for the labeled fixed in vitro capacitated sperm sample.

In one such embodiment, the method may further include the steps of: comparing the ratio for the labeled fixed in vitro non-capacitated sperm to a ratio of labeled fixed in vitro non-capacitated sperm having a known fertility status; and comparing the ratio for the labeled fixed in vitro capacitated sperm to a ratio of labeled fixed in vitro capacitated sperm having a known fertility status.

In one embodiment disclosed herein is a method for determining male fertility status. In one embodiment, the method includes the steps of: obtaining a first portion of a sperm sample from a male that has been exposed to in vitro non-capacitating conditions, fixed in a fixative for at least: one hour, two hours, four hours, eight hours, twelve hours, eighteen hours or twenty four hours, and treated with a labeling molecule for $G_{M1}$ localization patterns, wherein the labeling molecule has a detectable label; obtaining a second portion of the sperm sample that has been exposed to in vitro capacitating conditions, fixed in a fixative, and treated with the labeling molecule for $G_{M1}$ localization patterns; identifying more than one $G_{M1}$ labeled localization patterns for the labeled fixed in vitro non-capacitated sperm sample and the labeled fixed in vitro capacitated sperm sample, said $G_{M1}$ labeled localization patterns being an apical acrosome (AA) $G_{M1}$ localization pattern, an acrosomal plasma membrane (APM) $G_{M1}$ localization pattern, a Lined-Cell $G_{M1}$ localization pattern and all other labeled $G_{M1}$ localization patterns; comparing the labeled $G_{M1}$ localization patterns for the labeled fixed in vitro non-capacitated sperm sample to the labeled $G_{M1}$ localization patterns for the labeled fixed in vitro capacitated sperm sample; based on the comparison, assigning the apical acrosome (AA) $G_{M1}$ localization pattern and the acrosomal plasma membrane (APM) $G_{M1}$ localization pattern to a capacitated state and assigning the Lined-Cell $G_{M1}$ localization pattern and all other labeled $G_{M1}$ localization patterns to a non-capacitated state; and characterizing a fertility status of the male based on the identified $G_{M1}$ labeled localization patterns for the labeled fixed in vitro non-capacitated sperm sample and the labeled fixed in vitro capacitated sperm sample. In one embodiment, the characterizing step comprises the steps of: determining a fertility threshold associated with a percentage of [(AA $G_{M1}$ localization patterns plus APM $G_{M1}$ localization patterns)/total $G_{M1}$ localization patterns] for the labeled fixed in vitro capacitated sperm sample; wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is standard deviation below the reference mean percentage indicates fertile; less than a percentage that is one standard deviation below the reference mean percentage and greater than a percentage that is two standard deviations below the reference mean percentage indicates sub-fertile; less than a percentage that is two standard deviations below the reference mean percentage indicates infertile; comparing the percentage of [(AA $G_{M1}$ localization patterns plus APM $G_{M1}$ localization patterns)/total $G_{M1}$ localization patterns] for the labeled fixed in vitro capacitated sperm sample to the reference percentage of

[(AA $G_{M1}$ localization patterns plus APM $G_{M1}$ localization patterns)/total $G_{M1}$ localization patterns] and identifying the fertility threshold based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal male fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In some embodiments, the identifying step is repeated until the number of Lined-Cell $G_{M1}$ localization patterns is substantially constant. In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, determining the number of Lined-Cell $G_{M1}$ localization patterns, for the labeled fixed in vitro non-capacitated sperm until the number is less than: 25%, 20%, 15% or 10% of the total number of labeled cells; or ranges from 2% to 25%; 2% to 20%; 2 to 15%; 2 to 10%; 2 to 5% of the total number of labeled cells.

In one embodiment of such method, the method further includes the steps of: determining the number of each $G_{M1}$ labeled localization patterns for a predetermined number of the labeled fixed in vitro non-capacitated sperm sample and the labeled fixed in vitro capacitated sperm sample, and calculating a ratio for a sum of the number of AA $G_{M1}$ localization patterns and number of APM $G_{M1}$ localization patterns over a sum of the total number of $G_{M1}$ localization patterns for each of the labeled fixed in vitro non-capacitated sperm sample and the labeled fixed in vitro capacitated sperm sample.

In one such embodiment, the characterizing step may further include the steps of: comparing the ratio for the labeled fixed in vitro capacitated sperm sample to ratios of $G_{M1}$ localization patterns of in vitro capacitated sperm for males having a known fertility status; and comparing the ratio for the labeled fixed in vitro non-capacitated sperm sample to ratios of $G_{M1}$ localization patterns in vitro non-capacitated sperm for males having a known fertility status.

In one embodiment disclosed herein is a method for determining male fertility status. In one embodiment, the method includes the steps of: exposing, in vitro, a sperm sample from a male to capacitating conditions; fixing the capacitated sperm sample with a fixative for at least: one hour, two hours, four hours, eight hours, twelve hours, eighteen hours or twenty four hours, treating the fixed in vitro capacitated sperm sample with a labeling molecule for $G_{M1}$ localization patterns, wherein the labeling molecule has a detectable label; identifying more than one $G_{M1}$ labeled localization patterns for the labeled fixed in vitro capacitated sperm sample, said $G_{M1}$ labeled localization patterns being an apical acrosome (AA) $G_{M1}$ localization pattern, an acrosomal plasma membrane (APM) $G_{M1}$ localization pattern, a Lined-Cell $G_{M1}$ localization pattern and all other labeled $G_{M1}$ localization patterns; assigning the apical acrosome (AA) $G_{M1}$ localization pattern and the acrosomal plasma membrane (APM) $G_{M1}$ localization pattern to a capacitated state and assigning the Lined-Cell $G_{M1}$ localization pattern and all other labeled $G_{M1}$ localization patterns to a non-capacitated state; and characterizing a fertility status of the male. In one embodiment, the characterizing step comprises the steps of: determining a fertility threshold associated with a percentage of [(AA $G_{M1}$ localization patterns plus APM $G_{M1}$ localization patterns)/total $G_{M1}$ localization patterns] for the labeled fixed in vitro capacitated sperm sample; wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates fertile; less than a percentage that is one standard deviation below the reference mean percentage and greater than a percentage that is two standard deviations below the reference mean percentage indicates sub-fertile; less than a percentage that is two standard deviations below the reference mean percentage indicates infertile; comparing the percentage of [(AA $G_{M1}$ localization patterns plus APM $G_{M1}$ localization patterns)/total $G_{M1}$ localization patterns] for the labeled fixed in vitro capacitated sperm sample to the reference percentage of [(AA $G_{M1}$ localization patterns plus APM $G_{M1}$ localization patterns)/total $G_{M1}$ localization patterns] and identifying the fertility threshold based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than one standard deviation below the reference mean percentage indicates abnormal male fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In one embodiment, prior to the exposing steps, a semen sample is treated to decrease semen viscosity using a wide orifice pipette made of non-metallic material and using a reagent that does not damage sperm membrane chosen from the various reagents that are used to decrease semen viscosity. In some embodiments, the membrane damaging reagent is selected from the group consisting of (i) a protease; (ii) a nuclease (iii) a mucolytic agent; (iv) a lipase; (v) an esterase and (vi) glycoside hydrolases. In some embodiments, the identifying step is repeated until the number of Lined-Cell $G_{M1}$ localization patterns is substantially constant. In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, determining the number of Lined-Cell $G_{M1}$ localization patterns, for the labeled fixed in vitro non-capacitated sperm until the number is less than: 25%, 20%, 15% or 10% of the total number of labeled cells; or ranges from 2% to 25%; 2% to 20%; 2 to 15%; 2 to 10%; 2 to 5% of the total number of labeled cells. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

In one embodiment of such method, the method may further include the steps of: comparing the ratio of $G_{M1}$ localization patterns to ratios of $G_{M1}$ localization patterns for males having a known fertility status. In one embodiment, the known fertility status corresponds to fertile males. In another embodiment, the known fertility status corresponds to infertile males. In one such embodiment, the comparing step includes the steps of: determining the number of each $G_{M1}$ labeled localization patterns for a predetermined number of the labeled fixed in vitro capacitated sperm sample, and calculating a ratio for a sum of the number of AA $G_{M1}$ localization patterns and number of APM $G_{M1}$ localization patterns over a sum of the total number of $G_{M1}$ labeled localization patterns.

In one embodiment disclosed herein is a method for determining male fertility status. In one embodiment, the method includes the steps of: obtaining a first portion of a sperm sample from a male that has been exposed to in vitro capacitating conditions, fixed in a fixative for at least: one hour, two hours, four hours, eight hours, twelve hours, eighteen hours or twenty four hours, and stained with a labeling molecule for $G_{M1}$ localization patterns, wherein the labeling molecule has a detectable label; identifying more than one $G_{M1}$ labeled localization patterns for the labeled fixed in vitro capacitated sperm sample, said $G_{M1}$ localization patterns being an apical acrosome (AA) $G_{M1}$ localization pattern, an acrosomal plasma membrane (APM) $G_{M1}$ localization pattern, a Lined-Cell $G_{M1}$ localization pattern and all other labeled $G_{M1}$ localization patterns; assigning the apical acrosome (AA) $G_{M1}$ localization pattern and the acrosomal plasma membrane (APM) $G_{M1}$ localization pattern to a capacitated state and assigning the Lined-Cell $G_{M1}$ localization pattern and all other labeled $G_{M1}$ localization patterns to a non-capacitated state; and characterizing a fertility status of the male. In one embodiment, the characterizing step comprises the steps of: determining a fertility threshold associated with a percentage of [(AA $G_{M1}$ localization patterns plus APM $G_{M1}$ localization patterns)/total $G_{M1}$ localization patterns] for the labeled fixed in vitro capacitated sperm sample; wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates fertile; less than a percentage that is one standard deviation below the reference mean percentage and greater than a percentage that is that is two standard deviations below the reference mean percentage indicates sub-fertile; less than a percentage that is two standard deviations below the reference mean percentage indicates infertile; comparing the percentage of [(AA $G_{M1}$ localization patterns plus APM $G_{M1}$ localization patterns)/total $G_{M1}$ localization patterns] for the labeled fixed in vitro capacitated sperm sample to the reference percentage of [(AA $G_{M1}$ localization patterns plus APM $G_{M1}$ localization patterns)/total $G_{M1}$ localization patterns] and identifying the fertility threshold based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal male fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In some embodiments, the identifying step is repeated until the number of Lined-Cell $G_{M1}$ localization patterns is substantially constant. In one such embodiment, after the identifying step is performed, determining the number of Lined-Cell $G_{M1}$ localization patterns, for the labeled fixed in vitro capacitated sperm until the number is less than 5%, less than 3% of the total number of labeled cells; or ranges from 1% to 5%, 2 to 5% of the total number of labeled cells. In another such embodiment, after the identifying step is performed, determining the number of Lined-Cell $G_{M1}$ localization patterns, for the labeled fixed in vitro non-capacitated sperm until the number is less than: 25%, 20%, 15% or 10% of the total number of labeled cells; or ranges from 2% to 25%; 2% to 20%; 2 to 15%; 2 to 10%; 2 to 5% of the total number of labeled cells.

In one embodiment of such method, the method may further include the steps of: comparing the ratio of $G_{M1}$ localization patterns to ratios of $G_{M1}$ localization patterns for males having a known fertility status. In one embodiment, the known fertility status corresponds to fertile males. In another embodiment, the known fertility status corresponds to infertile males. In one such embodiment, the comparing step includes the steps of: determining the number of each $G_{M1}$ labeled localization patterns for a predetermined number of the labeled fixed in vitro capacitated sperm sample, and calculating a ratio for a sum of the number of AA $G_{M1}$ localization patterns and number of APM $G_{M1}$ localization patterns over a sum of the total number of $G_{M1}$ labeled localization patterns.

In one embodiment disclosed herein is a method for determining male fertility status. In one embodiment, the method includes the steps of: obtaining a sperm sample, wherein at least a portion of the sperm sample has been exposed to in vitro capacitating conditions to obtain in vitro capacitated sperm, has been exposed to a fixative for at least: one hour, two hours, four hours, eight hours, twelve hours, eighteen hours or twenty four hours, and has been stained for $G_{M1}$, obtaining values for one or more semen parameters of the sperm sample; determining a Cap-Score of the labeled fixed in vitro capacitated sperm sample based on one or more $G_{M1}$ labeled localization patterns, said $G_{M1}$ labeled localization patterns being an apical acrosome (AA) $G_{M1}$ localization pattern, a post-acrosomal plasma membrane (APM) $G_{M1}$ localization pattern, a Lined-Cell $G_{M1}$ localization pattern and all other labeled $G_{M1}$ localization patterns; and calculating a male fertility index (WI) value of the male based on the determined CAP score and the one or more obtained semen parameters. In one embodiment, the one or more semen parameters of the sperm sample are selected from the group consisting of volume of the original sperm sample, concentration of sperm, motility of sperm, and morphology of sperm.

An embodiment disclosed herein is a method for determining male fertility status. In one embodiment, the method comprises the following steps. A sample of in vitro capacitated sperm cells is treated with a fluorescence label. One or more capacitated-fluorescence images is obtained wherein the images display one or more $G_{M1}$ localization patterns associated with fluorescence labeled in vitro capacitated sperm cells. An apical acrosome (AA) $G_{M1}$ localization pattern and an acrosomal plasma membrane (APM) $G_{M1}$ localization pattern are each assigned to a capacitated state and a Lined-Cell $G_{M1}$ localization pattern and all other labeled $G_{M1}$ localization patterns are assigned to a non-capacitated state each displayed in the cap-fluorescence images. A number for $G_{M1}$ localization patterns is measured, the patterns comprising AA $G_{M1}$ localization pattern, APM $G_{M1}$ localization pattern, Lined-Cell $G_{M1}$ localization pattern and all other labeled $G_{M1}$ localization patterns, for the fluorescence labeled in vitro capacitated sperm cells, displayed in the capacitated-fluorescence images to determine a percentage of [(AA $G_{M1}$ localization patterns plus APM $G_{M1}$ localization patterns)/total $G_{M1}$ localization patterns]. A fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns] corresponding to: greater than a percentage that is one standard deviation below a reference mean percentage indicates fertile; less than a percentage that is one standard deviation below a reference mean percentage and greater than a percentage that is two standard deviations below a reference mean percentage indicates sub-fertile; less than a percentage that is two standard deviations below a reference mean percentage indicates infertile. The percentage of [(AA $G_{M1}$ localization patterns plus APM $G_{M1}$ localization patterns)/total $G_{M1}$ localization patterns] is compared to the reference percentage of [(AA $G_{M1}$ localization patterns plus APM $G_{M1}$ localization patterns)/total $G_{M1}$ localization patterns]. The fertility threshold is identified based on the comparison.

In another embodiment, a fertility threshold associated with a percentage of [(AA $G_{M1}$ localization patterns plus APM $G_{M1}$ localization patterns)/total $G_{M1}$ localization patterns] is determined, wherein a reference percentage of [(AA $G_{M1}$ localization patterns plus APM $G_{M1}$ localization patterns)/total $G_{M1}$ localization patterns], based on distribution statistics of a known fertile population corresponding to: greater than a percentage that is one standard deviation below the reference mean percentage indicates normal male fertility; less than a percentage that is one standard deviation below the reference mean percentage indicates abnormal fertility. The percentage of [(AA $G_{M1}$ localization patterns plus APM $G_{M1}$ localization patterns)/total $G_{M1}$ localization patterns] for the labeled fixed in vitro capacitated sperm sample is compared to the reference percentage of [(AA $G_{M1}$ localization patterns plus APM $G_{M1}$ localization patterns)/total $G_{M1}$ localization patterns]. The fertility threshold is identified based on the comparison.

In one such embodiment, the identifying step is also based on one or more of the following: patient demographics, reproductive status of female partner, sperm concentration, total motility, progressive motility, semen volume, semen pH, semen viscosity and/or sperm morphology and combinations thereof.

In various embodiments of the methods described herein, the sperm cells are treated in vitro with capacitation conditions for a capacitation time period of: at least one hour; at least 3 hours; at least 12 hours; at least 18 hours; at least 24 hours; for a capacitation time period ranging between 0.5 hours to 3 hours; 3 hours to 12 hours; 6 hours to 12 hours; 3 hours to 24 hours; 12 hours to 24 hours; or 18 hours to 24 hours.

In various embodiments of the methods described herein, the in vitro capacitated sperm cells are treated with a fixative for a fixative time period of: at least 0.5 hour; at least 3 hours; at least 12 hours; at least 18 hours; at least 24 hours; at least 30 hours; at least 36 hours; or at least 48 hours, for a fixation time period ranging between 0.5 hours to 3 hours; 3 hours to 12 hours; 6 hours to 12 hours; 3 hours to 18 hours; 6-18 hours; 6-24 hours; 12 hours to 24 hours; 18 hours to 24 hours; 18-30 hours; 18-36 hours; 24-30 hours; 24-26 hours; 18-48 hours; 24-48 hours; or 36-48 hours.

In various embodiments of the methods described herein, the more than one of $G_{M1}$ labeled localization patterns comprises AA $G_{M1}$ localization pattern, APM $G_{M1}$ localization pattern, Lined-Cell $G_{M1}$ localization pattern, intermediate (INTER) $G_{M1}$ localization pattern, post acrosomal plasma membrane (PAPM) $G_{M1}$ localization pattern, apical acrosome/post acrosome (AA/PA) $G_{M1}$ localization pattern, equatorial segment (ES) $G_{M1}$ localization pattern, and diffuse (DIFF) $G_{M1}$ localization pattern.

In one embodiment, exposing the first portion of the sperm sample to non-capacitating conditions and exposing the second portion of the sperm sample to capacitating conditions occur concurrently.

The male individual may be a human or a non-human animal. In the case of a non-human animal, identification of patterns that are correlated with fertility status can be carried out based on the teachings provided herein. Non-human animals include horse, cattle, dog, cat, swine, goat, sheep, deer, rabbit, chicken, turkey, various species of fish and various zoological species.

In one embodiment, the method of this disclosure provides a method for designating a male as likely infertile comprising obtaining $G_{M1}$ localization patterns (e.g., one or more of Lined-Cell, AA, APM, and all other $G_{M1}$ localization patterns) in the sperm from the individual and from a normal control that have been incubated under capacitating and non-capacitating conditions and optionally fixed, and comparing the $G_{M1}$ localization patterns. In the normal control, a statistically significant change in the percentage of sperm displaying certain localization patterns would be observed. If the same change is not observed in the sperm from the test individual, then the individual is designated as having an abnormal fertility status. In one embodiment, the patterns that are informative of normal and abnormal fertility status are localization patterns Lined-Cell, INTER, AA and/or APM. Thus, in a sample from an individual who is known to have a normal fertility status (which may be used as a control), there is a higher percentage of sperm exhibiting AA and/or APM localization patterns, and a lower percentage of sperm exhibiting the Lined-Cell and/or INTER localization pattern upon exposure to in vitro capacitating conditions when compared to the sperm being exposed to in vitro non-capacitating conditions. If no difference or no significant difference is observed in the percentages of one or more of these localization patterns upon exposure to in vitro capacitating conditions as compared to when the sperm is exposed to in vitro non-capacitating conditions, then the individual is designated as having fertility problems. In a variation of the above embodiment, the control may be from an individual known to be infertile or sub-fertile. In this embodiment, if the changes in $G_{M1}$ patterns from the test individual upon in vitro capacitation in the Lined-Cell, INTER, AA and/or APM localization patterns are the same as the control, then the individual can be deemed as sub-fertile or infertile.

In yet another variation of the above embodiment, the sample from a test individual may be evaluated without comparing to a control. If no change, or no significant change, is observed in the number of Lined-Cell, INTER, AA and/or APM patterns upon exposure to in vitro capacitating conditions, then the individual may be deemed as abnormal and may be designated for further testing, whereas if changes are observed such that Lined-Cell and/or INTER is decreased, AA is increased, and/or APM is increased, then the individual may be designated as having normal fertility.

In one embodiment, the method comprises analysis of $G_{M1}$ localization patterns to identify number of AA and APM patterns in sperm exposed to in vitro capacitating conditions. The number can be expressed as a percentage of one or more of the $G_{M1}$ distribution patterns relative to the total. In one embodiment, fertility is predicted based on a comparison of the number of AA and/or APM localization patterns against a predetermined fertility threshold, for example, the threshold (i.e., cut-off) level between individuals classified as infertile and sub-fertile, or the threshold level between individuals classified as sub-fertile and those classified as fertile.

In other embodiments, fertility thresholds may be determined by statistical analysis of the patterns found in sperm from a population of men, with known fertility. For the purposes of this application, a male is considered fertile or has normal male fertility if the male has a pregnant partner or has fathered a child within three years, using either natural conception or three or fewer cycles of intra-uterine insemination. For the purposes of this application, a male is consider sub-fertile if the male has failed to achieve a pregnancy with six to twelve months, without use of contraception, and required more than three cycles of intra-uterine insemination to achieve a pregnancy. For the purposes of this application, a male is considered infertile, if the male has failed to achieve a pregnancy within one year, without use of contraception, and failed to achieve a pregnancy using repeated cycles of intra-uterine insemination. For the purposes of this application, abnormal male fertility includes sub-fertile and infertile males.

Figure 4:
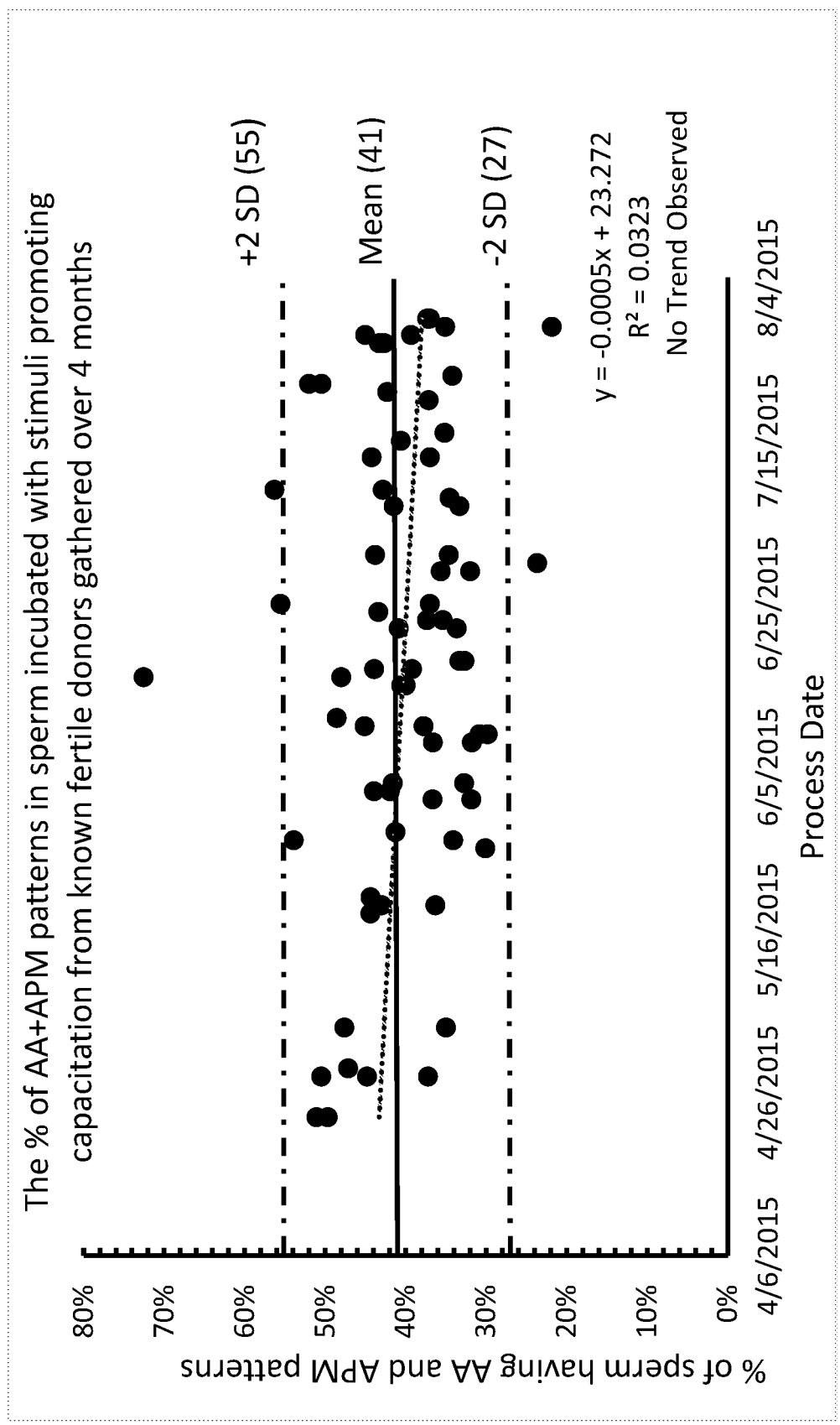
FIG. 4 shows the percentage of AA and APM localization patterns in sperm from known fertile donors incubated with stimuli promoting capacitation.

As shown in FIG. 4, 73 semen samples were obtained from 24 men known to be fertile. Their sperm was incubated with stimuli for capacitation, in this case 4 mM 2-hydroxy-propyl-βcyclodextrin, fixed with 0.01% paraformaldehyde (final concentration). The percentage of cells having patterns indicative of having capacitated (e.g., AA+APM) was assessed. The mean percentage of sperm having the AA and APM patterns was 41%, and two standard deviations from the mean was calculated as 27% and 55%.

Figure 5:
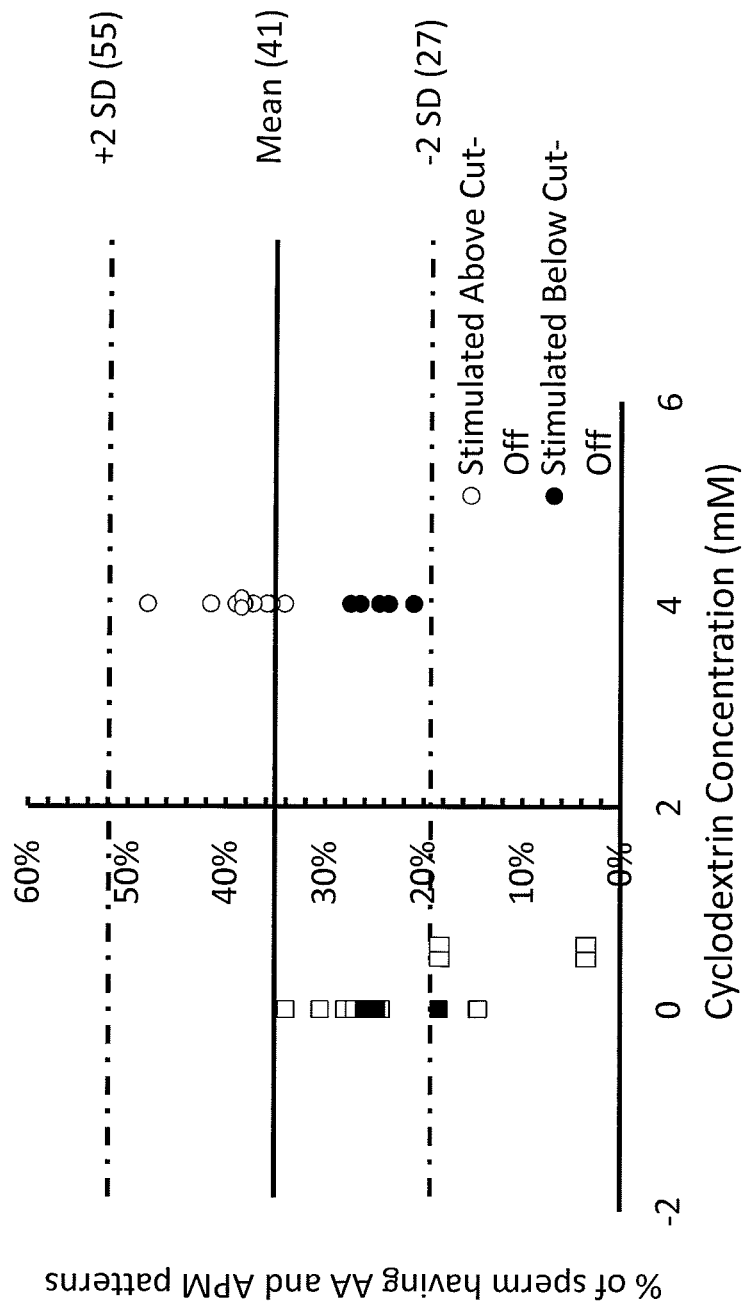
FIG. 5 shows a comparison of the percentage of AA and APM localization patterns in sperm from suspected subfertile/infertile donors with the statistical thresholds of fertile men.

$G_{M1}$ localization patterns in 14 samples from 14 men seeking medical evaluation of their fertility status were analyzed. The relative percentages of sperm having AA+APM localization patterns were compared against the statistical thresholds identified from the population of known fertile men (FIG. 5). There were no differences observed in the samples incubated under baseline (non-stimulating, non-capacitating conditions). However, 5 of the 14 men produced samples that showed low percentages of sperm with AA+APM patterns when incubated with 4 mM 2-hydroxy-propyl-β-cyclodextrin. These 5 samples all fell below two standard deviations from the mean. It is believed that approximately 30-50% of couples having difficulty conceiving have a component of male factor. These data fall within that expected range.

In one aspect, the present disclosure provides kits for determination of male fertility status. The kit comprises one or more of the following: a pipette having an orifice of sufficient size in diameter to prevent shearing of a sperm membrane, agents that can act as stimuli for in vitro capacitation, capacitating media, non-capacitating media, fixative, labeling reagents s for determining of $G_{M1}$ localization patterns, a diagram illustrating one or more $G_{M1}$ localization patterns of capacitated sperm and one of more $G_{M1}$ localization patterns of non-capacitated sperm. Such $G_{M1}$ localization patterns of capacitated sperm and $G_{M1}$ localization patterns of non-capacitated sperm are reflective of known fertility status. In such a kit embodiment, the fixative composition should not damage sperm membrane. In such embodiments, the reagent that can damage sperm membranes is chosen from the various reagents that are used to decrease semen viscosity. In some embodiments, the membrane damaging reagent includes one or more of a protease, a nuclease, a mucolytic agent, a lipase, an esterase and glycoside hydrolases. In another kit embodiment, the capacitating media and non-capacitating media, when applied in vitro to sperm cells, produce $G_{M1}$ localization patterns indicative of capacitated sperm and patterns indicative of non-capacitated sperm as reflected in the diagram.

In one embodiment, the kit comprises an agent having 4% cyclodextrin to stimulate capacitation.

In one embodiment, the capacitating media comprises: modified human tubal fluid with added 2-hydroxy-propyl-β-cyclodextrin so as to give a 3 mM final concentration; the non-capacitating media comprises modified human tubal fluid; the fixative is 1% paraformaldehyde; and the reagent for determining $G_{M1}$ patterns is cholera toxin's b subunit (15 μg/ml final concentration). In other embodiments, the final concentration of paraformaldehyde is 0.01%.

An exemplary kit comprises modified HTF medium with gentamicin buffered with HEPES (Irvine Scientific, reference 90126). No difference in $G_{M1}$ localization patterns, viability or sperm recovery, and capacitation was observed whether bicarbonate- or HEPES-buffered medium was used. Therefore, bicarbonate buffered media can also be used. Use of the HEPES-buffer enables the assay to be performed in clinics using air incubators or water baths, as opposed to only being compatible with $CO_2$ incubators. Similarly, adding supplemental proteins, whether commercial (HTF-SSS™, Irvine Scientific, or plasmanate), or powdered albumin did not alter recovery or viability, and favorably enhance capacitation status.

The exemplary kit can further comprise cell isolation media (such as Enhance S-Plus Cell Isolation Media, 90% from Vitrolife, reference: 15232 ESP-100-90%). The exemplary reagents, consumables and procedures were demonstrated to yield advantageous labeling of $G_{M1}$ on human sperm.

The exemplary kit can further comprise wide orifice pipette tips (200 μl large orifice tip, USA scientific, 1011-8400). The exemplary kit can further comprise wide orifice transfer pipettes (General Purpose Transfer Pipettes, Standard Bulb reference number: 202-20S. VWR catalog number 14670-147). In one embodiment, the pipette is non-metallic. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

The exemplary kit can further comprise 1.5 ml tubes (Treatment cap, noncap, CD) (USA Scientific 14159700)—one containing cyclodextrin in powdered form to stimulate capacitation, and one empty for noncapacitating conditions of media alone. In some embodiments, it is possible that the cyclodextrin will be found in a separate tube, to which medium will be added to make a stock solution, that itself would be added to the capacitating tube.

When isolating sperm from seminal plasma it is common for human andrology labs to collect sperm using density gradients. The exemplary kit can further comprise density gradient materials and/or instructions to remove the seminal plasma off the density gradient and then to collect the pelleted sperm using a fresh transfer pipette.

The exemplary kit can further comprise the fixative (such as 0.1% PFA), and optionally comprises informational forms (such as patient requisition form), labels and containers/bags/pouches and the like useful for shipping, storage or regulatory purposes. For example, the kit can contain a foil pouch, a biohazard bag with absorbent for mailing patient sample, a re-sealable bag with absorbent, and a foam tube place holder.

The exemplary kit can further include instructions describing any of the methods disclosed herein.

In another aspect, a method for measuring the fertility of a male individual is provided. The $G_{M1}$ localization assay can show whether sperm can capacitate, and therefore become competent to fertilize an egg. As described above, the assay may be scored as percentages of the morphologically normal sperm that have specific patterns of $G_{M1}$ localization in the sperm head. The APM and AA patterns increase as sperm respond to stimuli for capacitation. Cut-offs can be used to distinguish the relative fertility of the ejaculates, separating the semen samples into groups based on male fertility (e.g., distinguishing fertile from sub-fertile from infertile men). However, because sperm number, motility, and morphology can also influence male fertility, the present disclosure provides methods for creating an index of male fertility (the "male fertility index" or "MFI") that encompasses Cap-Score and one or more relevant semen parameters (e.g., number, motility, and morphology, etc.). Cap-Score (also referred to as $G_{M1}$ score) is the number of one or more $G_{M1}$ patterns. For example, a Cap-Score can be a number of one or more of Lined-Cell, INTER, AA, and APM. Different indices can be generated that emphasize specific semen parameters. For example, indexes according to the present disclosure include:

Cap-Score×% with progressive motility×absolute number;

Cap-Score×% morphologically normal sperm×absolute number;

Cap-Score×% total motility×absolute number×% morphologically normal sperm; and other variations or combinations of Cap-Score and these parameters, or other specific parameters including those obtained using CASA (computer assisted sperm analysis), such as: VSL (velocity straight line); STR (straightness); LIN (Linearity); VCL (curvilinear velocity); VAP (velocity average path); % motility; duration of motility; LHA (lateral head amplitude); WOB (wobble); PROG (progression); and BCF (Beat cross number), etc. See, e.g., World Health Organization, "WHO Laboratory Manual for the Examination and Processing of Human Sperm," (Fifth Ed. 2010).

The male fertility index may be embodied as a method for measuring the fertility status of a male individual. A sperm sample is obtained, wherein the sperm sample is from the individual being measured and wherein at least a portion of the sperm sample has been exposed to in vitro capacitating conditions, exposed to a fixative, and stained for $G_{M1}$, as described above. The values of one or more semen parameters are obtained for the sperm sample, such as, for example, the volume of the original sample from the individual, and/or the concentration, motility, and/or morphology of the sperm of the sample. An MFI is determined from the number of one or more $G_{M1}$ patterns (e.g., the "CAP" score) and the one or more obtained semen parameter values. In the examples used herein, the Cap-Score is the percentage of one or more $G_{M1}$ patterns under capacitating conditions at three hours, but other variants of Cap-Scores will be apparent in light of this disclosure (e.g., number at other time intervals, change in number of a $G_{M1}$ pattern in capacitated from non-capacitated, etc.)

In one embodiment, a male fertility index score may be calculated for a sample of men according to the following equation: Male Fertility Index/Fertility Group=$a+b_1 \ast x_1 + b_2 \ast x_2 + \ldots + b_m \ast x_m$ where a is a constant, $b_1$ through $b_m$ are regression coefficients and $x_1$ though $x_m$ are male fertility variables such as Cap-Score, motility, morphology, volume, and concentration. Discriminant function analysis may be used to determine which fertility variables discriminate between two or more naturally occurring groups. For example, to determine if an individual falls into a fertile, sub-fertile or in-fertile group, data would be collected for numerous fertility variables that describe sperm function and semen quality. A Discriminant Analysis may then be used to determine which variable(s) is/are the best predictors of fertility group and relatively how much each fertility variable should be weighted.

The male fertility index may be generated by a lab that reads the $G_{M1}$ localization assay. The lab may obtain a sperm sample, and a semen analysis corresponding to the sperm sample, from one or more facility (e.g., fertility clinic, sperm bank, etc.). Semen analysis information can be included on a card included with a $G_{M1}$ localization assay kit, sent electronically to the lab, and/or otherwise provided. In another exemplary embodiment, the lab obtains the Cap-Score of a sperm sample and also obtains the semen analysis information for the sperm sample. In one embodiment, the lab calculates the male fertility index based on the obtained Cap-Score and the obtained semen analysis data.

An exemplary method for identifying fertility status of a male comprises exposing sperm sample from the individual to in vitro non-capacitating and in vitro capacitating conditions. The sperm are fixed and a percentage of selected $G_{M1}$ patterns in the fixed sperm is determined. The percentage for different $G_{M1}$ patterns in sperm exposed to in vitro non-capacitating and in vitro capacitating conditions is compared. A change in the percentage of one or more selected $G_{M1}$ patterns in sperm exposed to in vitro capacitating conditions over sperm exposed to in vitro non-capacitating conditions is indicative of the fertility status of the individual. The selected $G_{M1}$ patterns can be Lined-Cell, INTER, AA and/or APM. In one embodiment, the fertility status of the individual is determined by calculating a ratio for a sum of the number of AA $G_{M1}$ localization patterns and number of APM $G_{M1}$ localization patterns over a sum of the total number of $G_{M1}$ labeled localization patterns for the capacitated sperm.

An exemplary method for identifying fertility status of a male comprises exposing a sperm sample from the individual to in vitro capacitating conditions. The sperm are fixed and a percentage of selected $G_{M1}$ patterns in the fixed sperm is determined. The percentage for different $G_{M1}$ patterns is compared to the percentage from a control, wherein the control sperm sample has been exposed to the same in vitro capacitating conditions and same fixative. A change in the percentage of one or more selected $G_{M1}$ patterns relative to the change in the control is indicative of different fertility status of the individual than the fertility status of the control. The $G_{M1}$ patterns can be Lined-Cell, INTER, AA and/or APM. In one embodiment, the fertility status of the individual is determined by calculating a ratio for a sum of the number of AA $G_{M1}$ localization patterns and number of APM $G_{M1}$ localization patterns over a sum of the total number of $G_{M1}$ labeled localization patterns for the capacitated sperm. In one embodiment, prior to the exposing steps, a semen sample is treated to decrease semen viscosity using a wide orifice pipette made of non-metallic material and using a reagent that does not damage sperm membrane chosen from the various reagents that are used to decrease semen viscosity. In some embodiments, the membrane damaging reagent is selected from the group consisting of (i) a protease; (ii) a nuclease (iii) a mucolytic agent; (iv) a lipase; (v) an esterase and (vi) glycoside hydrolases. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

In the exemplary method, the control can be a sperm sample from an individual who is known to have normal fertility status or an individual who is known to have abnormal fertility status. The control can be a value obtained from a dataset comprising a plurality of individuals, for example, a dataset comprising at least 50 individuals.

An exemplary method for identifying fertility status of a male as infertile, sub-fertile, or fertile, comprises exposing a sperm sample from the individual to in vitro capacitating conditions. $G_{M1}$ patterns in the sample are determined. The percentage of one or more $G_{M1}$ patterns is compared to a fertility threshold wherein a percentage less than the fertility threshold is indicative of fertility problems. For example, a percentage less than the fertility threshold can be indicative of a fertility status of infertile or sub-fertile. The $G_{M1}$ patterns can be Lined-Cell, INTER, AA and/or APM. In one embodiment, the fertility status of the individual is determined by calculating a ratio for a sum of the number of AA $G_{M1}$ localization patterns and number of APM $G_{M1}$ localization patterns over a sum of the total number of $G_{M1}$ labeled localization patterns for the capacitated sperm. In one embodiment, prior to the exposing steps, a semen sample is treated to decrease semen viscosity using a wide orifice pipette made of non-metallic material and using a reagent that does not damage sperm membrane chosen from the various reagents that are used to decrease semen viscosity. In some embodiments, the membrane damaging reagent is selected from the group consisting of (i) a protease; (ii) a nuclease (iii) a mucolytic agent; (iv) a lipase; (v) an esterase and (vi) glycoside hydrolases. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

The in vitro capacitating conditions in the exemplary methods can include exposure to i) bicarbonate and calcium ions, and ii) mediators of sterol efflux such as 2-hydroxypropyl-β-cyclodextrin, methyl-β-cyclodextrin, serum albumin, high density lipoprotein, phospholipids vesicles, fetal cord serum ultrafiltrate, fatty acid binding proteins, or liposomes. In the exemplary methods, exposure of the control to capacitating or non-capacitating conditions can be done in parallel with the test sample.

An exemplary method for identifying fertility status of a male as infertile, sub-fertile, or fertile, comprises exposing a sperm sample from the individual to capacitating conditions. The percentage of each $G_{M1}$ pattern in the sample is determined. The percentage of one or more $G_{M1}$ patterns is compared to an infertility threshold wherein a percentage less than the infertility threshold is indicative of fertility problems. The capacitating conditions in the exemplary method can include exposure to i) bicarbonate and calcium ions, and ii) mediators of sterol efflux such as 2-hydroxypropyl-β-cyclodextrin, methyl-β-cyclodextrin, serum albumin, high density lipoprotein, phospholipids vesicles, fetal cord serum ultrafiltrate, fatty acid binding proteins, or liposomes. The one or more $G_{M1}$ localization patterns can be Lined-Cell, INTER, AA and/or APM. In one embodiment, the fertility status of the individual is determined by calculating a ratio for a sum of the number of AA $G_{M1}$ localization patterns and number of APM $G_{M1}$ localization patterns over a sum of the total number of $G_{M1}$ labeled localization patterns for the capacitated sperm. In one embodiment, prior to the exposing steps, a semen sample is treated to decrease semen viscosity using a wide orifice pipette made of nonmetallic material and using a reagent that does not damage sperm membrane chosen from the various reagents that are used to decrease semen viscosity. In some embodiments, the membrane damaging reagent is selected from the group consisting of (i) a protease; (ii) a nuclease (iii) a mucolytic agent; (iv) a lipase; (v) an esterase and (vi) glycoside hydrolases. In some embodiments the wide orifice pipette has a gauge size of at least 18 gauge, 16 gauge or 14 gauge. In some embodiments, the wide orifice pipette has an orifice size of at least 1 mm, 1.2 mm or 1.4 mm.

The fertility threshold in the exemplary methods can be the AA+APM pattern percentage at which the fertility of a population ceases to substantially increase. For example, the fertility threshold can be a level of AA+APM at which more than 50% of the population are fertile; a level of AA+APM at which more than 60-85% of a population is fertile; or a level of AA+APM in the range of 35-40 (relative percentage of total $G_{M1}$ patterns), inclusive. The fertility threshold can be 38, 38.5, 39, or 39.5% AA+APM (relative to total $G_{M1}$ patterns).

An exemplary method may further comprise comparing the percentage of one or more $G_{M1}$ patterns to an infertility threshold wherein a percentage less than the infertility threshold is indicative of infertility. For example, the infertility threshold can be the AA+APM pattern percentage at which the fertility of a population begins to substantially increase; a level of AA+APM at which less than 50% of the population are fertile; a level of AA+APM at which more than 60-85% of a population is fertile; or a level of AA+APM in the range of 14-18 (relative percentage of total $G_{M1}$ patterns), inclusive. The infertility threshold can be 14, 14.5, 15, or 15.5% AA+APM (relative to total $G_{M1}$ patterns).

An exemplary method for identifying fertility status of a male comprises obtaining sperm samples, wherein the sperm samples are from the individual and wherein the sperm samples have been exposed to non-capacitating or capacitating conditions, fixed, and stained for $G_{M1}$. The number of selected $G_{M1}$ patterns in the sperm is determined. The percentage for different $G_{M1}$ patterns in sperm exposed to in vitro non-capacitating and in vitro capacitating conditions is compared. A change in the percentage of one or more selected $G_{M1}$ patterns in sperm exposed to in vitro capacitating conditions over sperm exposed to in vitro non-capacitating conditions is indicative of the fertility status of the individual. The $G_{M1}$ pattern can be selected from the group consisting of AA, APM, INTER, Lined-Cell and combinations thereof. In one embodiment, the fertility status of the individual is determined by calculating a ratio for a sum of the number of AA $G_{M1}$ localization patterns and number of APM $G_{M1}$ localization patterns over a sum of the total number of $G_{M1}$ labeled localization patterns for the capacitated sperm.

An exemplary method for identifying fertility status of a male individual comprises obtaining a sperm sample, wherein the sperm sample is from the individual and wherein the sperm sample has been exposed to in vitro capacitating conditions, has been fixed and has been stained for the presence of $G_{M1}$. A number of selected $G_{M1}$ patterns in the sperm is determined. The percentage for one or more different $G_{M1}$ patterns is compared to the percentage of patterns from a control or predetermined criteria. The control sperm sample has been exposed to the same in vitro capacitating conditions and same fixative. A change in the percentage of one or more selected $G_{M1}$ patterns relative to the change in the control is indicative of different fertility status of the individual than the fertility status of the control.

An exemplary method for identifying fertility status of a male individual comprises obtaining a sperm sample, wherein the sperm sample is from the individual, and wherein the sperm sample has been exposed to in vitro capacitating conditions, has been fixed, and has been stained for $G_{M1}$ patterns. The $G_{M1}$ localization patterns in the sample are determined. The percentage of one or more $G_{M1}$ patterns is compared to an infertility threshold wherein a percentage less than the infertility threshold is indicative of fertility problems.

An exemplary method for measuring the fertility status of a male individual comprises obtaining a sperm sample, wherein the sperm sample is from the individual, and wherein the sperm sample has been exposed to in vitro capacitating conditions, has been exposed to a fixative, and has been stained for $G_{M1}$. Values are obtained for one or more of volume of the original sample, and concentration, motility, and morphology of the sperm in the original sample. A Cap-Score of the sperm sample is determined as the percentage of one or more $G_{M1}$ localization patterns in the sample. A male fertility index (MFI) value of the individual is calculated based on the determined Cap-Score and the one or more obtained volume, concentration, motility, and morphology. For example, the MFI value can be calculated by multiplying the Cap-Score, the volume, the concentration, the motility value, and the morphology value. The motility can be a percentage of the sperm which are motile. The morphology can be a percentage of the sperm that are morphologically normal.

An exemplary method for measuring the fertility status of a male individual comprises obtaining a Cap-Score of a sperm sample of the individual as the percentage of one or more $G_{M1}$ localization patterns in the sample. Values are obtained for one or more of volume of the original sample, and concentration, motility, and morphology of the sperm in the original sample. A male fertility index (MFI) value of the individual is calculated based on the determined Cap-Score and the one or more obtained volume, concentration, motility, and morphology.

The invention is further described through the following illustrative examples, which are not to be construed as restrictive.

Example 1

This example provides demonstration of $G_{M1}$ localization patterns obtained with human sperm. Ejaculated sperm were collected from male donors, and allowed to liquefy for 20 mins at 37° C., and then volume, initial count, motility and morphology assessments were performed. 1 ml of the semen sample was layered on top of 1 ml of a density gradient (90% Enhance-S; Vitrolife, San Diego, Calif., USA) in a 15 ml conical tube. The tube was centrifuged at 300×g for 10 minutes. The bottom 1 ml fraction was transferred to a new 15 ml tube and then resuspended in 4 ml of mHTF. This was centrifuged at 600×g for 10 minutes. The supernatant was removed and the pellet of sperm was resuspended in 0.5 ml of mHTF. The washed sperm were then evaluated for concentration and motility. Equal volumes of sperm were then added to two tubes, such that the final volume of each tube was 300 µl, and the final concentration of sperm was 1,000,000/ml. The first tube contained mHTF (non-capacitating condition) and the second tube contained mHTF plus 2-hydroxy-propyl-β-cyclodextrin at a final concentration of 3 mM (capacitating condition). Sperm were incubated for varying lengths of time, but 3 hours was typically used. These incubations were performed at 37° C.

At the end of the incubation period, the contents of each tube were mixed gently, and 18 µl from each tube was removed and transferred to separate microcentrifuge tubes. 2 µl of 1% (weight/volume) paraformaldehyde was added to achieve a final concentration of 0.1%. In another embodiment, 0.1% (weight/volume) paraformaldehyde was added to achieve a final concentration of 0.01%. These tubes were mixed gently and incubated at room temperature for 15 minutes, at which time 0.3 µl of 1 mg/ml cholera toxin b subunit was added. The contents of the two tubes were again mixed gently and allowed to incubate for an additional 5 minutes at room temperature. From each tube, 5 µl was removed and placed on a glass slide for evaluation by fluorescence microscopy. To provide a counter-stain, speeding determination of focal planes and increasing longevity of the fluorescence signal, 3 µl of DAPI/Antifade was sometimes added.

Figures 2A, 2B, 2C:
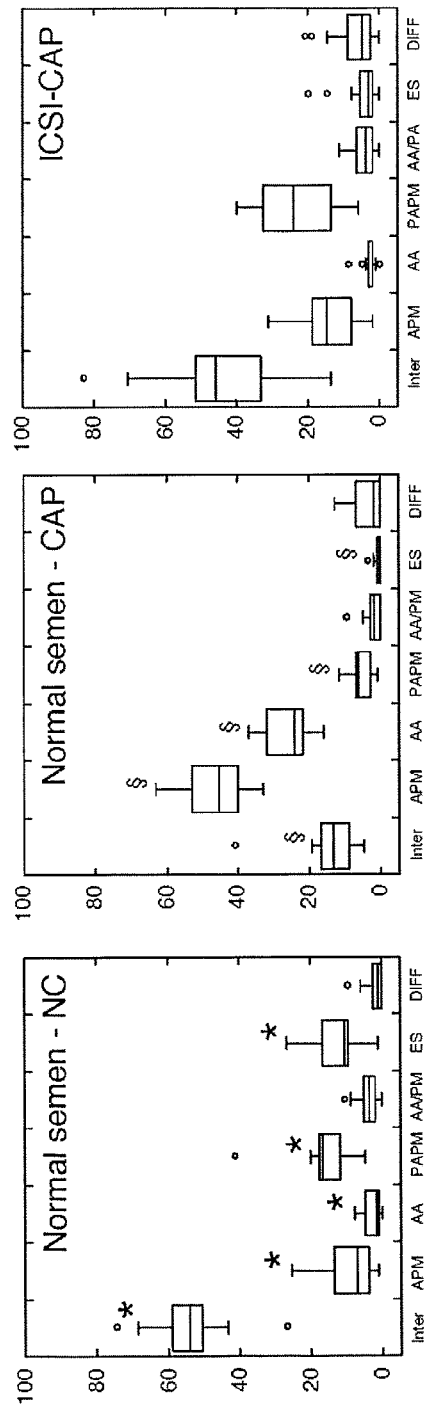
FIG. 2A shows the relative distributions of the INTER, APM, AA, PAPM, AA/PA, ES, and DIFF localization patterns of $G_{M1}$ in normal human sperm under non-capacitating conditions.
FIG. 2B shows the relative distributions of the INTER, APM, AA, PAPM, AA/PA, ES, and DIFF localization patterns of $G_{M1}$ in normal human sperm under capacitating conditions.
FIG. 2C shows the relative distributions of the INTER, APM, AA, PAPM, AA/PA, ES, and DIFF localization patterns of $G_{M1}$ in human sperm from infertile males under capacitating conditions.

As shown in FIG. 2, localization patterns of $G_{M1}$ in normal human sperm reflect response to capacitating conditions. Full response is seen only in men with normal fertility; the responsive pattern was largely reduced or absent in men with unexplained infertility who have failed on previous attempts at intrauterine insemination (IUI) or in vitro fertilization (IVF). FIG. 1 shows the $G_{M1}$ patterns in human sperm. However, for the purpose of the diagnostic assay, patterns reflecting abnormalities such as PAPM, AA/PA, ES, and DIFF can be grouped for ease of analysis. FIGS. 2A-2C show the relative distributions of the different patterns in normal semen incubated under non-capacitating conditions (NC; FIG. 2A), or capacitating conditions (CAP; FIG. 2B). A reduction in INTER pattern is seen in normal semen upon exposure to CAP (FIG. 2C), while significant increases in the AA pattern and the APM pattern are also seen. In comparison with these normal data, sperm from a group of men known to have unexplained infertility were also subjected to the $G_{M1}$ assay. In these sperm, there was almost no increase in the AA pattern or the APM pattern under capacitating conditions.

Example 2

In this example, clinical histories of 34 patients were studied to perform a close analysis of their $G_{M1}$ assay scores relative to history of ever achieving clinical evidence of pregnancy. A male patient was defined as "fertile" if a patient couple achieved some evidence of fertilization/clinical pregnancy (even if limited to biochemical evidence or a sac without heartbeat on ultrasound) within 3 or fewer cycles.

Analysis of the data for these 34 patients revealed that if one applied a cut-off of 40% (APM+AA) for the score of the capacitated samples at the 3 hour time point, then 7/8 who "passed" (having a score of 39.5% or greater), were found to have been designated "fertile" (87.5%). Of the 26 who "failed" (having a score of 39.4 or less), only 3/26 had evidence of clinical pregnancy (11.5%). (see Table 1 below).

If one reduces the cutoff, it would be predicted that more people who are clinically sub-fertile will get a passing score and the percentage that pass the assay and are fertile within 3 cycles should go down. Interestingly, the result was not a smooth gradient or continuous curve in terms of fertility (as defined by the ≤=3 cycle criterion). That is, whether one failed the assay as defined at 40 or 35 didn't correlate with any significant change in chance of fertility, which was always low (between 11.5-14.3%). Conversely, passing the assay at 35 vs 40 corresponded with a very large difference in chances of fertility (ranging from 53.8-87.5%, respectively). To reinforce and reiterate this point, a change in 5% of the combined APM+AA percentages corresponded with over a 30% change in history of fertility.

These results suggest that male fertility is more like a "step function," in which ranges of scores for the male fertility assay correspond with categorizations of "fertile," "sub-fertile" or "infertile," rather than small changes in scores equating with correspondingly small but continuous changes in male fertility (chance of achieving clinical pregnancy). These data indicate strongly that a score of roughly 38.5-40 would be the cut-off between designations of "sub-fertile" or "fertile." Further examination of the data suggest that a cut-off of <14.5% could be used as a designation of likely "infertile."

| Cut-Off | Fertile Defined on Conceiving Within ≤/=3 cycles | |
| --- | --- | --- |
| 39.5 | Pass | 8 (7/8 fertile = 87.5%) |
| | Fail | 26 (3/26 fertile = 11.5%) |
| 38.5 | Pass | 8 (7/8 fertile = 87.5%) |
| | Fail | 26 (3/26 fertile = 11.5%) |
| 37.5 | Pass | 11 (7/11 fertile = 63.6%) |
| | Fail | 23 (3/23 fertile = 13.0%) |
| 36.5 | Pass | 11 (7/11 fertile = 63.6%) |
| | Fail | 23 (3/23 fertile = 13.0%) |
| 35.5 | Pass | 13 (7/13 fertile = 53.8%) |
| | Fail | 21 (3/21 fertile = 14.3%) |

Summarizing data for these men, who were all similar in terms of average semen parameters, suggest the following ranges (based on absolute scores): Infertile: <14.5, sub-fertile: 14.5-38.4, fertile: ≥38.5.

Figure 3:
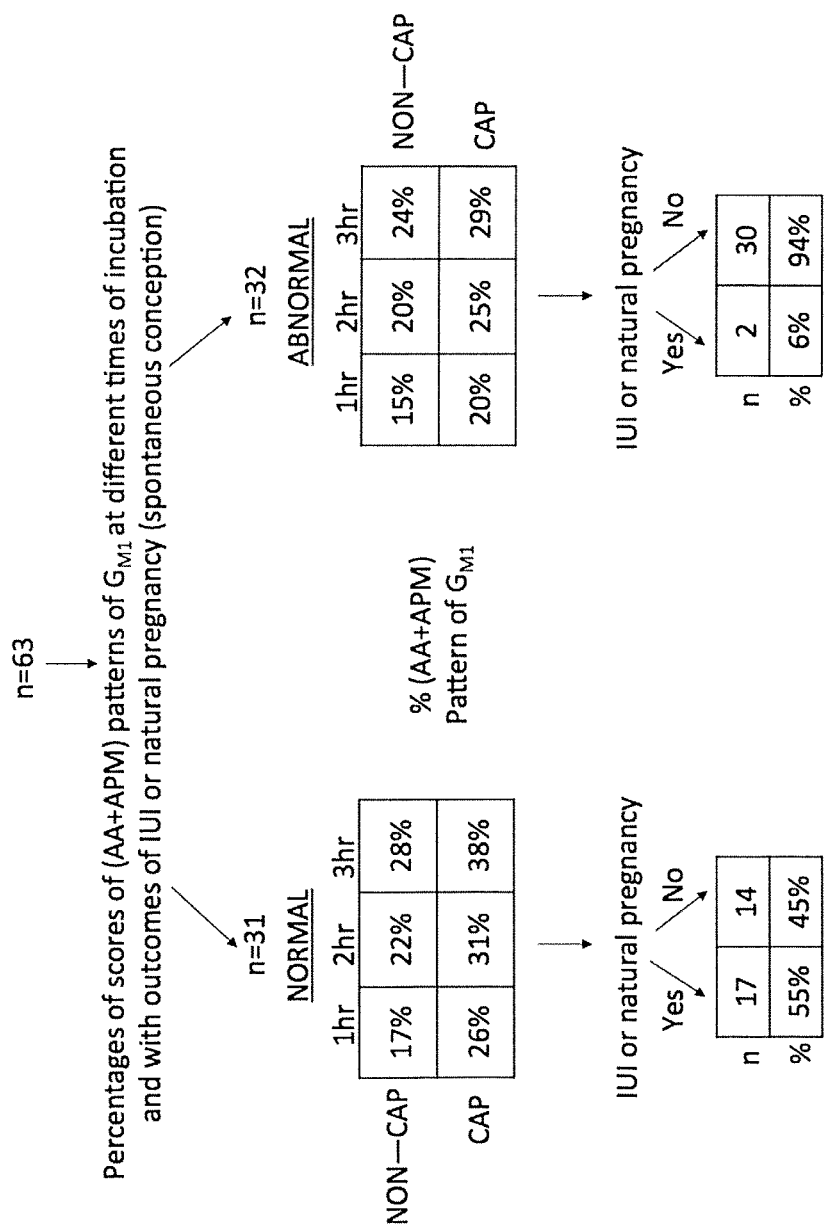
FIG. 3 shows the relative number of the combined APM and AA localizations patterns as a function of time of incubation in human sperm for a group normal males and in human sperm for a group infertile males, under capacitating conditions and non-capacitating conditions, and the clinical outcomes for each group of males.

Alternatively, one can evaluate the fertility of a sample by comparing the change in relative number of the APM and/or AA patterns over the time of incubation under capacitating conditions, or against the relative number observed under non-capacitating conditions. For example, one could compare the APM+AA relative number after 3 hours of incubation in capacitating conditions with the relative number of those patterns at the start of incubation. In yet another embodiment, one might compare the change in APM and/or AA frequencies with results obtained from successive time points (such as 1, 2, and 3 hours). In effect, one can plot the relative frequencies on the Y axis and time points on the X axis, and evaluate the slope or rate of change of the increasing number of one or more of the INTER, APM and/or AA samples under non-capacitating and capacitating conditions. When this approach to the analysis was performed in a group of 63 patients, 31 men with scores matching the normal reference group were identified, with baseline $G_{M1}$ patterns of 17%-22%-28% in non-capacitating and 26%-31%-38% in capacitating media, respectively over 1, 2, and 3 hours of incubation (see FIG. 3). 32 men with below reference values of 15%-20%-24% in non-capacitating and 20%-25%-29% in capacitating media were identified. Semen analysis parameters of number, motility and percent normal morphology (using strict WHO criteria) were comparable between the two groups. The population with normal range $G_{M1}$ patterns had an intrauterine insemination (IUI) pregnancy rate of 45.2% (14/31) of which 8 (25.8%) generated at least one fetal heartbeat. Three additional couples in this group became pregnant on their own. For men with below-reference $G_{M1}$ patterns, the IUI clinical pregnancy rate was only 6.3% (2/32; P=0.03). In this cohort, 13 underwent ICSI and 6 became pregnant (46.2%).

Example 3

Sperm cells were treated as described in Example 1 but incubated in fixative for 24 hours. The labeled sperm cells were then evaluated by fluorescence microscopy. A new $G_{M1}$ localization pattern, Lined-Cells was identified as illustrated in FIGS. 6A, 6B, 6C and 6D. In Lined-cells, as illustrated in FIG. 6A, there is $G_{M1}$ signal at the bottom of the equatorial segment/top of the post acrosomal region, and at the plasma membrane overlying the acrosome. The signal is evenly distributed in the post acrosome/equatorial region and the plasma membrane overlying the acrosome. There is also a band at the equatorial segment that lacks signal. As illustrate in FIG. 6B, the signal at the plasma membrane overlying the acrosome is brighter than the signal at the post acrosome/equatorial band. As illustrated in FIGS. 6C and 6D, the signal found at the post acrosome/equatorial band is brighter than the signal at the plasma membrane overlying the acrosome.

Sperm cells from a single donor were washed, incubated under both capacitating (Stim) and non-capacitating (Non-Stim) conditions and then scored both on day 0 (maintained in fix for approximately 5 hours) and day 1 (maintained in fix for approximately 27.5 hours). There was little change in the percentage of Lined-cells from day 0 to day 1 for the Stim treatment. In contrast, the percent of lined cells from day 0 to day 1 increased from 3 to 22% for the Non-Stim treatment. In conjunction with this change, there was a subsequent decrease in INTER from 76 to 51%. These data are consistent with lined cell patterns developing on day 1 from cells having an inter pattern on day 0.

TABLE 1

| | % AA | % APM | % Inter | % Lined Cells | % Other |
| --- | --- | --- | --- | --- | --- |
| Non-Stim day 0 | 0 | 16 | 76 | 3 | 6 |
| Stim day 0 | 7 | 19 | 62 | 4 | 8 |
| Non-Stim day 1 | 4 | 14 | 51 | 22 | 10 |
| Stim day 1 | 4 | 24 | 53 | 3 | 16 |

Example 4

Cells from a single donor were washed, incubated under both capacitating (Stim) and non-capacitating (Non-Stim) conditions and then scored both on day 0 (maintained in fix for approximately 4 hour) and day 1 (maintained in fix for approximately 25 hours). Since few lined cells were observed on day 0, similar Cap-Scores were obtained on day 0 with or without including the number of Lined-cells for determining the Cap-Scores. However, with the emergence of Lined-cells on day 1, different Cap-Score™ values could be obtained depending on how the Lined-cells were interpreted. For example, when Lined-cells were treated as Non-Capacitated, similar Cap-Scores™ were obtained for both the Stim and non-Stim treatments. However, if the Lined-cells were treated as capacitated, separated or removed from the Cap-Score™ calculation, greater Cap-Scores were obtained for the Non-Stim treatment than for the Stim treatment. Having larger Cap-Score™ values for the Non-Stim treatment makes no sense, as these sperm cells were incubated under basal conditions and thus would not have shown $G_{M1}$ patterns associated with capacitation. These observations provide further complementary evidence that Lined-cells represent a non-capacitated state and should be treated as such when calculating Cap-Score™.

TABLE 2

| | Cap-Score ™ computed with: | | | |
|---|---|---|---|---|
| | Lined cells as Non-Capacitated | Lined cells as Capacitated | Lined cells separated | Lined Cells removed |
| Non-Stim day 0 | 18 | 20 | 20 | 19 |
| Stim day 0 | 28 | 31 | 30 | 29 |
| Non-Stim day 1 | 35 | 52 | 52 | 42 |
| Stim day 1 | 36 | 39 | 38 | 37 |

Example 5

Forty different semen samples, from 18 unique donors were washed, the sperm were incubated under both capacitating (Stim) and non-capacitating (Non-Stim) conditions and then scored both on day 0 and day 1. A significant correlation is observed between Stim Cap-Score™ values obtained on day 0 and day 1 when Lined-cells are treated as non-capacitated (r=0.32; n=40; p<0.05). In contrast, no correlation is observed between day 0 and day 1 when Lined-cells are treated as capacitated, separated into either capacitated or non-capacitated bins based on $G_{M1}$ localization pattern, or simply removed from the Cap-Score™. These observations support the view that the Lined-cells localization pattern develops as sperm are maintained overnight and that on day 0 these sperm exhibit an inter/non-capacitated pattern. The treatment of Lined-cells as non-capacitated, stabilizes the Cap-Score™ over time and is consistent with this pattern reflecting cells that are infertile. What's more, these data demonstrate that interpretation of the Lined-cells as non-capacitated is applicable to the population. Nonetheless, the appearance of Lined-cells on day 1 is donor dependent. This raises the possibility that observation of these Lined-cells may provide additional information about these donors and the ability of their sperm to fertilize.

Although the present disclosure has been described with respect to one or more particular embodiments, it will be understood that other embodiments of the present disclosure may be made without departing from the spirit and scope of the present disclosure, and such other embodiments are intended to be within the scope of this disclosure.

We claim:

1. A method comprising:
   treating a fixed in vitro capacitated sperm sample from a male with a labeling molecule for GM1 localization patterns, wherein the labeling molecule has a detectable label;
   identifying more than one GM1 labeled localization patterns for the labeled fixed in vitro capacitated sperm sample, wherein the GM1 labeled localization patterns comprises an apical acrosome (AA) GM1 localization pattern, an acrosomal plasma membrane (APM) GM1 localization pattern, a Lined-Cell GM1 localization pattern, a post acrosomal plasma membrane (PAMP) GM1 localization pattern, an apical acrosome/post acrosome (AA/PA) GM1 localization pattern, an intermediate (INTER) GM1 localization pattern, an equatorial segment (ES) GM1 localization pattern, and a diffuse (DIFF) GM1 localization pattern;
   assigning the apical acrosome (AA) GM1 localization pattern and the acrosomal plasma membrane (APM) GM1 localization pattern to a capacitated state;
   determining a fertility threshold corresponding to a ratio of GM1 localization patterns being (i) the number of GM1 labeled localization patterns assigned to the capacitated state over (ii) the number of GM1 labeled localization patterns comprising AA, APM, Lined-Cell, PAMP, AA/PA, INTER, ES and DIFF GM1 localization patterns;
   comparing the fertility threshold to a reference value; and
   determining a fertility status of the male based on said comparison identifying the male subject for an appropriate assisted reproductive treatment.

2. The method of claim 1, wherein:
   the fertility threshold is a percentage of [(AA GM1 localization patterns plus APM GM1 localization patterns)/total GM1 localization patterns] for the labeled fixed in vitro capacitated sperm sample; and
   the reference value of [(AA GM1 localization patterns plus APM GM1 localization patterns)/total GM1 localization patterns] is based on distribution statistics of a known fertile population wherein a fertility threshold that is (i) greater than a percentage that is one standard deviation below the reference value indicates fertile; (ii) less than a percentage that is one standard deviation below the reference mean percentage value and greater than a percentage that is two standard deviations below a reference value indicates sub-fertile; and (iii) less than a percentage that is two standard deviations below the reference value indicates infertile.

3. The method of claim 1, further comprising the step of:
   comparing the ratio of GM1 localization patterns in the in vitro capacitated sperm sample from the male to ratios of GM1 localization patterns in sperm samples for males having a known fertility status.

4. The method of claim 3, wherein the comparing step comprises:
   determining the number of each GM1 labeled localization patterns for a predetermined number of the labeled fixed in vitro capacitated sperm sample, and
   calculating a ratio for a sum of the number of AA GM1 localization patterns and number of APM GM1 localization patterns over a sum of the total number of GM1 labeled localization patterns.

5. The method of claim 1, wherein the capacitated sperm sample is prepared by exposing the sperm sample from the male to one or more of bicarbonate ions, calcium ions, and a mediator of sterol efflux.

6. The method of claim 5, wherein the mediator of sterol efflux is 2-hydroxy-propyl-cyclodextrin, methyl- -cyclodextrin, serum albumin, high density lipoprotein, phospholipid vesicles, fetal cord serum ultrafiltrate, fatty acid binding proteins, or liposomes.

7. The method of claim 6, wherein the mediator of sterol efflux is 2-hydroxy-propyl- -cyclodextrin.

8. The method of claim 3, wherein the known fertility status corresponds to fertile males.

9. The method of claim 3, wherein known fertility status corresponds to infertile males.

10. The method of claim 1, wherein the fixed in vitro capacitated sperm sample is prepared by adding a fixative to the in vitro capacitated sperm sample, wherein the fixative comprises paraformaldehyde, glutaraldehyde or combinations thereof.

11. The method of claim 1, wherein the labeling molecule for GM1 localization patterns is fluorescent labeled cholera toxin b subunit.

12. The method of claim 1, wherein the step of identifying more than one GM1 labeled localization patterns is performed from 2 to 24 hours after the capacitating sperm sample.

13. The method of claim 1, further comprising the step of: prior to the exposing step, treating the sperm sample to decrease semen viscosity using a wide orifice pipette made of non-metallic material and using a reagent that does not damage sperm membranes.

14. A method comprising:
obtaining a portion of a fixed in vitro capacitated sperm sample from a male that has been stained with a labeling molecule for GM1 localization patterns, wherein the labeling molecule has a detectable label;
identifying more than one GM1 labeled localization patterns for the labeled fixed in vitro capacitated sperm sample, wherein the GM1 localization patterns comprises an apical acrosome (AA) GM1 localization pattern, an acrosomal plasma membrane (APM) GM1 localization pattern, a Lined- Cell GM1 localization pattern, a post acrosomal plasma membrane (PAMP) GM1 localization pattern, an apical acrosome/post acrosome (AA/PA) GM1 localization pattern, an intermediate (INTER) GM1 localization pattern, an equatorial segment (ES) GM1 localization pattern, and a diffuse (DIFF) GM1 localization pattern;
assigning the apical acrosome (AA) GM1 localization pattern and the acrosomal plasma membrane (APM) GM1 localization pattern to a capacitated state;
determining a fertility threshold corresponding to a ratio of GM1 localization patterns being (i) the number of GM1 labeled localization patterns assigned to the capacitated state over (ii) the number of GM1 labeled localization patterns comprising of AA, APM, Lined- Cell, PAMP, AA/PA, INTER, ES and DIFF GM1 localization patterns;
comparing the fertility threshold to a reference value; and
determining a fertility status of the male based on said comparison identifying the male subject for an appropriate assisted reproductive treatment.

15. The method of claim 14, wherein:
the fertility threshold is a percentage of [(AA GM1 localization patterns plus APM GM1 localization patterns)/total GM1 localization patterns] for the labeled fixed in vitro capacitated sperm sample;
wherein a reference value of [(AA GM1 localization patterns plus APM GM1 localization patterns)/total GM1 localization patterns] is based on distribution statistics of a known fertile population wherein a fertility threshold that is (i) greater than a percentage that is one standard deviation below the reference mean percentage indicates fertile; (ii) less than a percentage that is one standard deviation below the reference mean percentage and greater than a percentage that is two standard deviations below a reference mean percentage indicates sub-fertile; and (iii) less than a percentage that is two standard deviations below the reference mean percentage indicates infertile.

16. The method of claim 14, further comprising the step of:
comparing the ratio of GM1 localization patterns in the in vitro capacitated sperm sample from the male to ratios of GM1 localization patterns for males having a known fertility status.

17. The method of claim 16, wherein the comparing step comprises:
determining the number of each GM1 labeled localization patterns for a predetermined number of the labeled fixed capacitated sperm sample, and
calculating a ratio for a sum of the number of AA GM1 localization patterns and number of APM GM1 localization patterns over a sum of the total number of GM1 labeled localization patterns.

18. The method of claim 14, wherein the capacitated sperm sample is prepared by exposing the sperm sample from the male to one or more of bicarbonate ions, calcium ions, and a mediator of sterol efflux.

19. The method of claim 18, wherein the mediator of sterol efflux is 2-hydroxy-propyl- -cyclodextrin, methyl- -cyclodextrin, serum albumin, high density lipoprotein, phospholipid vesicles, fetal cord serum ultrafiltrate, fatty acid binding proteins, or liposomes.

20. The method of claim 19, wherein the mediator of sterol efflux is 2-hydroxy-propyl-β-cyclodextrin.

21. The method of claim 16, wherein the known fertility status corresponds to fertile males.

22. The method of claim 16, wherein the known fertility status corresponds to infertile males.

23. The method of claim 14, wherein the fixed in vitro capacitated sperm sample is prepared by adding a fixative to the in vitro capacitated sperm sample, wherein the fixative the fixative comprises paraformaldehyde, glutaraldehyde or combinations thereof.

24. The method of claim 14, wherein the labeling molecule for GM1 localization patterns is fluorescent labeled cholera toxin b subunit.

25. The method of claim 14, wherein the step of identifying more than one GM1 labeled localization patterns is identifying step is performed from 2 to 24 hours after capacitating the sperm sample.

26. The method of claim 14, further comprising the step of: prior to the obtaining step, treating a semen sample to decrease semen viscosity using a wide orifice pipette made of non-metallic material and using a reagent that does not damage sperm membranes.

* * * * *